US010478431B2

(12) United States Patent
Weinberger

(10) Patent No.: US 10,478,431 B2
(45) Date of Patent: Nov. 19, 2019

(54) METHODS FOR TREATING A CYTOMEGALOVIRUS INFECTION

(71) Applicant: The J. David Gladstone Institutes, San Francisco, CA (US)

(72) Inventor: Leor S. Weinberger, Oakland, CA (US)

(73) Assignee: The J. David Gladstone Institutes, San Francisco, CA (US)

( * ) Notice: Subject to any disclaimer, the term of this patent is extended or adjusted under 35 U.S.C. 154(b) by 0 days.

(21) Appl. No.: 15/527,662

(22) PCT Filed: Nov. 24, 2015

(86) PCT No.: PCT/US2015/062528
§ 371 (c)(1),
(2) Date: May 17, 2017

(87) PCT Pub. No.: WO2016/086060
PCT Pub. Date: Jun. 2, 2016

(65) Prior Publication Data

US 2017/0360778 A1 Dec. 21, 2017

Related U.S. Application Data

(60) Provisional application No. 62/084,954, filed on Nov. 26, 2014.

(51) Int. Cl.

| | |
|---|---|
| ***A61K 31/496*** | (2006.01) |
| ***A61K 45/06*** | (2006.01) |
| ***A01N 1/02*** | (2006.01) |
| ***A61K 31/522*** | (2006.01) |
| ***A61K 31/662*** | (2006.01) |
| ***A61K 31/675*** | (2006.01) |
| ***A61K 31/7056*** | (2006.01) |

(52) U.S. Cl.
CPC .......... *A61K 31/496* (2013.01); *A01N 1/0215* (2013.01); *A61K 31/522* (2013.01); *A61K 31/662* (2013.01); *A61K 31/675* (2013.01); *A61K 31/7056* (2013.01); *A61K 45/06* (2013.01)

(58) Field of Classification Search
CPC .............. A61K 31/496; A61K 31/7056; A61K 31/675; A61K 31/662; A61K 31/522; A61K 45/06; A01N 1/0215
See application file for complete search history.

(56) References Cited

U.S. PATENT DOCUMENTS

| | | | |
|---|---|---|---|
| 5,360,795 | A | 11/1994 | Townsend et al. |
| 5,968,933 | A | 10/1999 | Denny et al. |
| 7,642,275 | B2 | 1/2010 | Bressi et al. |
| 7,683,185 | B2 | 3/2010 | Joel et al. |
| 7,732,475 | B2 | 6/2010 | Bressi et al. |
| 7,737,184 | B2 | 6/2010 | Belvedere et al. |
| 7,741,494 | B2 | 6/2010 | Bressi et al. |
| 7,772,245 | B2 | 8/2010 | Anandan et al. |
| 7,795,304 | B2 | 9/2010 | Belvedere et al. |
| 7,799,825 | B2 | 9/2010 | Ferrigno et al. |
| 7,803,800 | B2 | 9/2010 | Minucci et al. |
| 7,842,727 | B2 | 11/2010 | Lan-Hargest et al. |
| 7,842,835 | B2 | 11/2010 | Kozikowski et al. |
| 2005/0234033 | A1 | 10/2005 | Anandan et al. |
| 2010/0291003 | A1 | 11/2010 | Rajagopal et al. |
| 2010/0292320 | A1 | 11/2010 | Melvin, Jr. |
| 2010/0317739 | A1 | 12/2010 | Brown et al. |
| 2014/0212945 | A1 | 7/2014 | Disney |

FOREIGN PATENT DOCUMENTS

| | | |
|---|---|---|
| WO | WO 1990005550 | 5/1990 |
| WO | WO 1996001833 | 1/1996 |
| WO | WO 2000020401 | 4/2000 |
| WO | WO 2002030879 | 4/2002 |
| WO | WO 2003082288 | 10/2003 |
| WO | WO 2005011661 | 2/2005 |
| WO | WO 2005108367 | 11/2005 |
| WO | WO 2006017214 | 2/2006 |
| WO | WO 2006017215 | 2/2006 |
| WO | WO 2006123121 | 11/2006 |
| WO | WO 2013026947 | 2/2013 |

OTHER PUBLICATIONS

Bansal et al., Bioorg. Med. Chem., 2012, 20, p. 6208-6236. (Year: 2012).*
Kuntz-Simon et al., J. Gen. Virol., 1995, 76, p. 1409-1415. (Year: 1995).*
Greaves et al., J. Virol., 1998, 72(1), p. 366-379. (Year: 1998).*
Smith et al., Cell Host & Microbe, 2010, 8, p. 284-291. (Year: 2010).*
Acharya et al. (2005) "Rational development of histone deacetylase inhibitors as anticancer agents: a review"; *Mol. Pharmacol.* 68; pp. 917-932.
Baraldi et al. (2004) "DNA minor groove binders as potential antitumor and antimicrobial agents"; *Med. Res. Rev.* 24:475-528.
Bolovan-Fritts, C., and Wiedeman, J.A. (2001) "Human cytomegalovirus strain Toledo lacks a virus-encoded tropism factor required for infection of aortic endothelial cells"; *J Infect Dis* 184; pp. 1252-1261.
Bolovan-Fritts, C.A., et al (2004) "Human cytomegalovirus-specific CD4+-T-cell cytokine response induces fractalkine in endothelial cells"; *J Virol* 78(23); pp. 13173-13181.

(Continued)

*Primary Examiner* — Jonathan S Lau
(74) *Attorney, Agent, or Firm* — Michael B. Rubin; Bozicevic, Field & Francis LLP

(57) ABSTRACT

The present disclosure provides a method for inhibiting cytomegalovirus (CMV) replication in a cell infected with CMV, the method comprising contacting the cell with a bisbenzimidazole compound. The present disclosure provides a method of treating a CMV infection in an individual, the method comprising administering to the individual an effective amount of a bisbenzimidazole compound.

20 Claims, 23 Drawing Sheets

Specification includes a Sequence Listing.

(56) References Cited

OTHER PUBLICATIONS

Bouchain et al. (2003) "Development of potential antitumor agents. Synthesis and biological evaluation of a new set of sulfonamide derivatives as histone deacetylase inhibitors"; *J. Med. Chem.* 46; pp. 820-830.

Bouchain et al (2003) "Novel hydroxamate and anilide derivatives as potent histone deacetylase inhibitors: synthesis and antiproliferative evaluation"; *Curr. Med. Chem.* 10; pp. 2359-2372.

Bresnahan, W.A., and Shenk, T.E. (2000) "UL82 virion protein activates expression of immediate early viral genes in human cytomegalovirus-infected cells"; *Proc Natl Acad Sci U S A* 97; pp. 14506-14511.

Cuevas-Bennett, C., and Shenk, T. (2008) "Dynamic histone H3 acetylation and methylation at human cytomegalovirus promoters during replication in fibroblasts"; *J Virol* 82; pp. 9525-9536.

Dickey et al. "Hoechst .Increases MY-mediated Transgene Expression in Airway Epithelia by Inducing the CMV Promoter" *The Journal of Gene Medicine*, vol. 14, Iss. 6, Jun. 27, 2012; pp. 366-373.

Dokmanovic et al. (2007) "Histone deacetylase inhibitors: overview and perspectives"; *Mol. Cancer. Res.* 5; pp. 981-989.

Dull, T., et al. (1998) "A third-generation lentivirus vector with a conditional packaging system"; *J Virol* 72; pp. 8463-8471.

Finn et al. (2005) "Novel Sulfonamide Derivatives as Inhibitors of Histone Deacetylase"; *Helv. Chim. Acta* 88; pp. 1630-1657.

Gravatt et al. (1994) "DNA-directed alkylating agents. 6. Synthesis and antitumor activity of DNA minor groove-targeted aniline mustard analogues of pibenzimol (Hoechst 33258)"; *J Med. Chem.* 37; pp. 4338-4345.

Kraut et al. (1991) "Phase II study of pibenzimol in pancreatic cancer. A Southwest Oncology Group study"; *Invest. New Drugs* 9; pp. 95-96.

Lavoie et al. (2001) "Design and synthesis of a novel class of histone deacetylase inhibitors"; *Bioorg. Med. Chem. Lett.* 11: pp. 2847-2850.

Lilja, A.E., et al. (2008) "Functional genetic analysis of rhesus cytomegalovirus: Rh01 is an epithelial cell tropism factor"; *J Virol* 82(5); pp. 2170-2181.

Mann et al. (2001) "A new class of symmetric bisbenzimidazole-based DNA minor groove-binding agents showing antitumor activity"; *J. Med. Chem.* 44(2); pp. 138-144.

Marson et al. (2004) "Stereodefined and polyunsaturated inhibitors of histone deacetylase based on (2E,4E)-5-arylpenta-2,4-dienoic acid hydroxyamides"; *Bioorg. Med. Chem. Lett.* 14; pp. 2477-2481.

Meier, J.L. (2001) "Reactivation of the human cytomegalovirus major immediate-early regulatory region and viral replication in embryonal NTera2 cells: role of trichostatin A, retinoic acid, and deletion of the 21-base-pair repeats and modulator"; *J Virol* 75(4); pp. 1581-1593.

Moorman, N.J., et al. (2008) "Human cytomegalovirus protein UL38 inhibits host cell stress responses by antagonizing the tuberous sclerosis protein complex"; *Cell Host Microbe* 3(4); pp. 253-262.

Nelson et al. (2007) "Non-covalent ligand/DNA interactions: minor groove binding agents"; *Mutation Res.* 623; pp. 24-40.

Nevels, M., et al (2004) "SUMOylation of the human cytomegalovirus 72-kilodalton IE1 protein facilitates expression of the 86-kilodalton 1E2 protein and promotes viral replication"; *J Virol* 78(14); pp. 7803-7812.

Orr, M.T., et al (2010) "Unlicensed' natural killer cells dominate the response to cytomegalovirus infection"; *Nat Immunol* 11; pp. 321-327.

Patel et al. (1991) "Phase I-II study of pibenzimol hydrochloride (NSC 322921) in advanced pancreatic carcinoma"; *Invest. New Drugs* 9; pp. 53-57.

Teng, M.W.,et al (2012) "An endogenous accelerator for viral gene expression confers a fitness advantage"; *Cell* 151(7); pp. 1569-1580.

Warming, S., et al. (2005) "Simple and highly efficient BAC recombineering using galK selection"; *Nucleic Acids Res* 33; e36; pp. 1-12.

Wong et al. (1994) "Transcriptional regulation of differentiation, selective toxicity and ATGCAAAT binding of bisbenzimidazole derivatives in human melanoma cells"; *Biochem. Pharmacol.* 47:827-837.

Yu, D., et al (2002) "Construction of a self-excisable bacterial artificial chromosome containing the human cytomegalovirus genome and mutagenesis of the diploid TRL/IRL13 gene"; *J Virol* 76(5); pp. 2316-2328.

Dorjsuren D et al (2006) "Chemical library screen for novel inhibitors of Kaposi's sarcoma-associated herpesvirus processive DNA synthesis"; Antiviral Research. Elsevier BV. NL., vo 69,No. 1.; pp. 9-23.

Lombardy R L et al (1996) "Synthesis and DNA Interactions of Benzimidazole Dications Which Have Activity Against Opportunistic Infections"; Journal of Medicinal Chemistry. American Chemical Society, vol. 39. No. 7; pp. 1452-1462.

* cited by examiner

ARPE-19 LM2ig reporter line
Side scatter
250K
200K
150K
100K
50K
0
MIEP
IE2
ires
GFP+
50.3
GFP
+ BB33258 (20uM)
GFP+
90.1
GFP
GFP
(%ON)
100
75
50
25
0
no drug
VPA/TNF/TSA
BB33258
(20uM)
N-Tera2 latency assay
Latent Reactivation
(% AD169 reactivation in
latent NTera2
cells by
IE gene expression)
no drug
VPA/TNF/TSA
BB33258 (20uM)

| | 1 | 2 | 3 | 4 | 5 | 6 | 7 | 8 | 9 | 10 | 11 | 12 |
|---|---|---|---|---|---|---|---|---|---|---|---|---|
| A | h1 | h2 | h3 | h4 | h5 | h6 | h7 | h8 | h9 | h10 | h11 | h12 |
| B | h13 | h14 | h15 | h16 | h17 | | rh1 | rh2 | rh3 | rh4 | rh5 | rh6 |
| C | rh7 | rh8 | rh9 | rh10 | rh11 | rh12 | rh13 | rh14 | rh15 | rh16 | rh17 | |
| D | m1 | m2 | m3 | m4 | m5 | m6 | m7 | m8 | m9 | m10 | m11 | m12 |
| E | m13 | m14 | m15 | m16 | m17 | | c1 | c2 | c3 | c4 | c5 | c6 |
| F | c7 | c8 | c9 | c10 | c11 | c12 | c13* | c14* | c15* | c16* | c17 | |
| G | b1 | b2 | b3 | b4 | b5 | b6 | b7 | b8 | b9 | b10 | b11 | b12 |
| H | b13 | b14 | b15 | b16 | b17 | | hcmv | rhcmv | mcmv | cg | | |

Figure 16

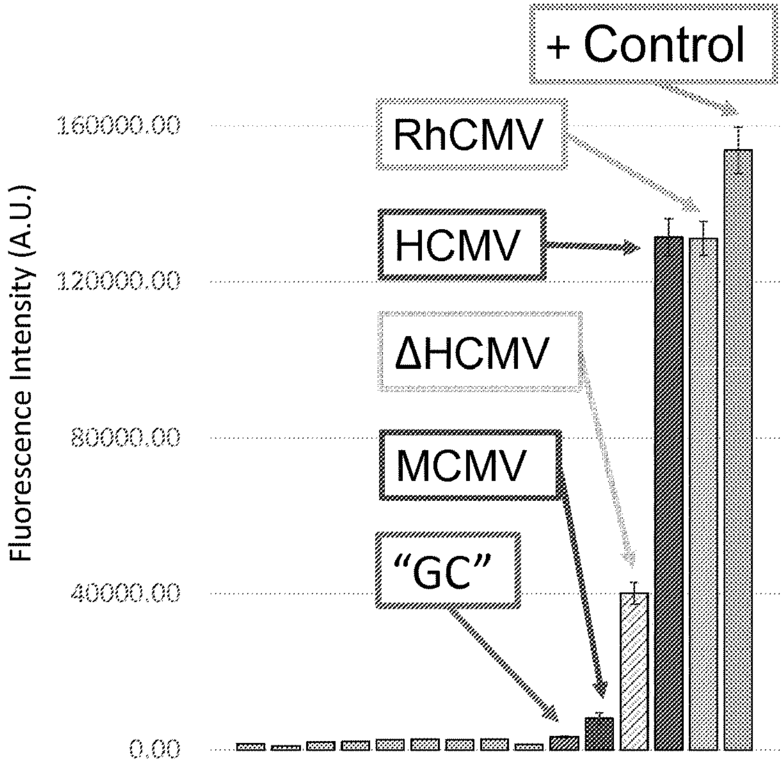

BB33258 Binding Motif

| | -14 | -13 | -12 | -11 | -10 | -9 | -8 | -7 | -6 | -5 | -4 | -3 | -2 | -1 |
|---|---|---|---|---|---|---|---|---|---|---|---|---|---|---|
| hCMV | T | C | G | **T** | **T** | **T** | **A** | G | T | G | A | A | C | C |
| ΔhCMV | T | C | a* | g* | g* | T | A | G | T | G | A | A | C | C |
| rhCMV | T | C | G | **T** | **T** | **T** | **A** | G | G | G | A | A | C | C |
| mCMV | C | C | A | G | C | G | T | C | G | G | T | A | C | C |
| Neg Control | G | C | G | C | G | C | G | C | G | C | G | C | G | C |
| Pos Control | C | G | C | **A** | **A** | **A** | **A** | **T** | **T** | **T** | **T** | G | C | G |

Light grey in the top four rows indicates homology with HCMV CRS sequence. Dark grey in 2nd, 3rd, and 4th rows indicates divergence from HCMV CRS sequence. Grey sequences in the bottom two rows are artificial controls and were chosen from representative literature. Bolded and underlined bases may indicate BB33258 binding sites according to both literature and these binding results.

Gel Shift Assay of IE2-crs

Figure 21:Feedback Inhibitor BB33258 Breaks IE2 Circuit & Amplifies IE2 Expression Levels in clinically derived CMV isolate TB40E
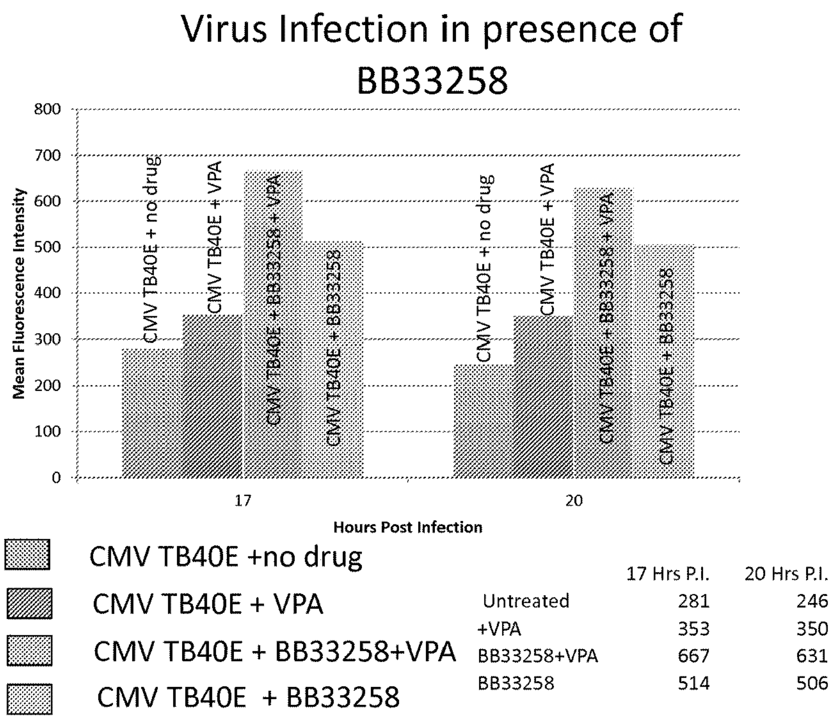
| | 17 Hrs P.I. | 20 Hrs P.I. |
|---|---|---|
| Untreated | 281 | 246 |
| +VPA | 353 | 350 |
| BB33258+VPA | 667 | 631 |
| BB33258 | 514 | 506 |

Figure 22:Feedback Inhibitor BB33258 Results in Virus Fitness Loss for clinically derived isolate of CMV (TB40E)

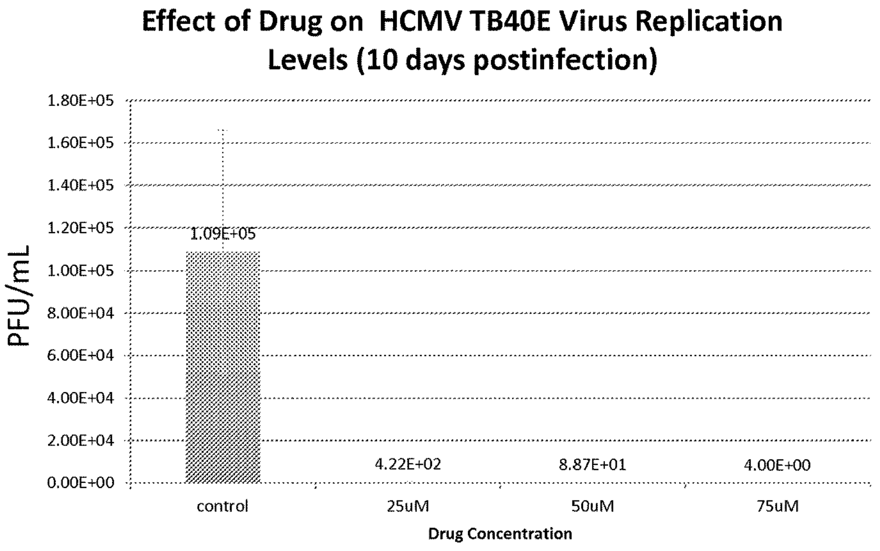

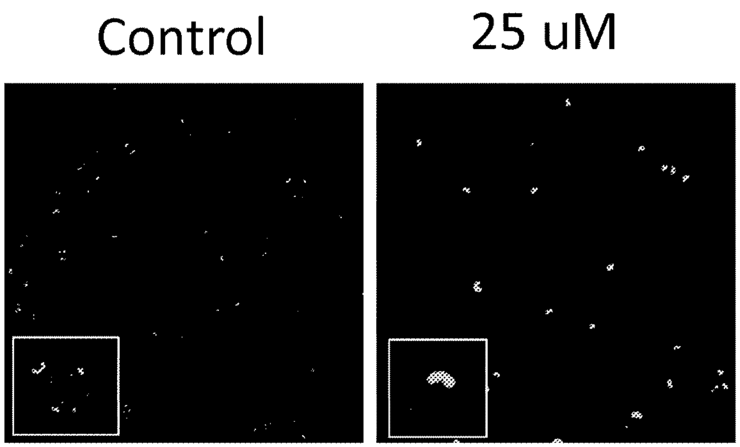

Detection of virus infection where IE2-YFP positive cells show drug treatment (right panel image) inhibits cell to cell spread. (Cells show more CPE with drug treatment and appear more distorted and larger.) Infection at MOI of 1 on confluent epithelial cell monolayers. Images on day 5, post infection.

Figure 23: Hoescht 33258 (20 μM) inhibits HCMV infection across a wide range of virus concentrations
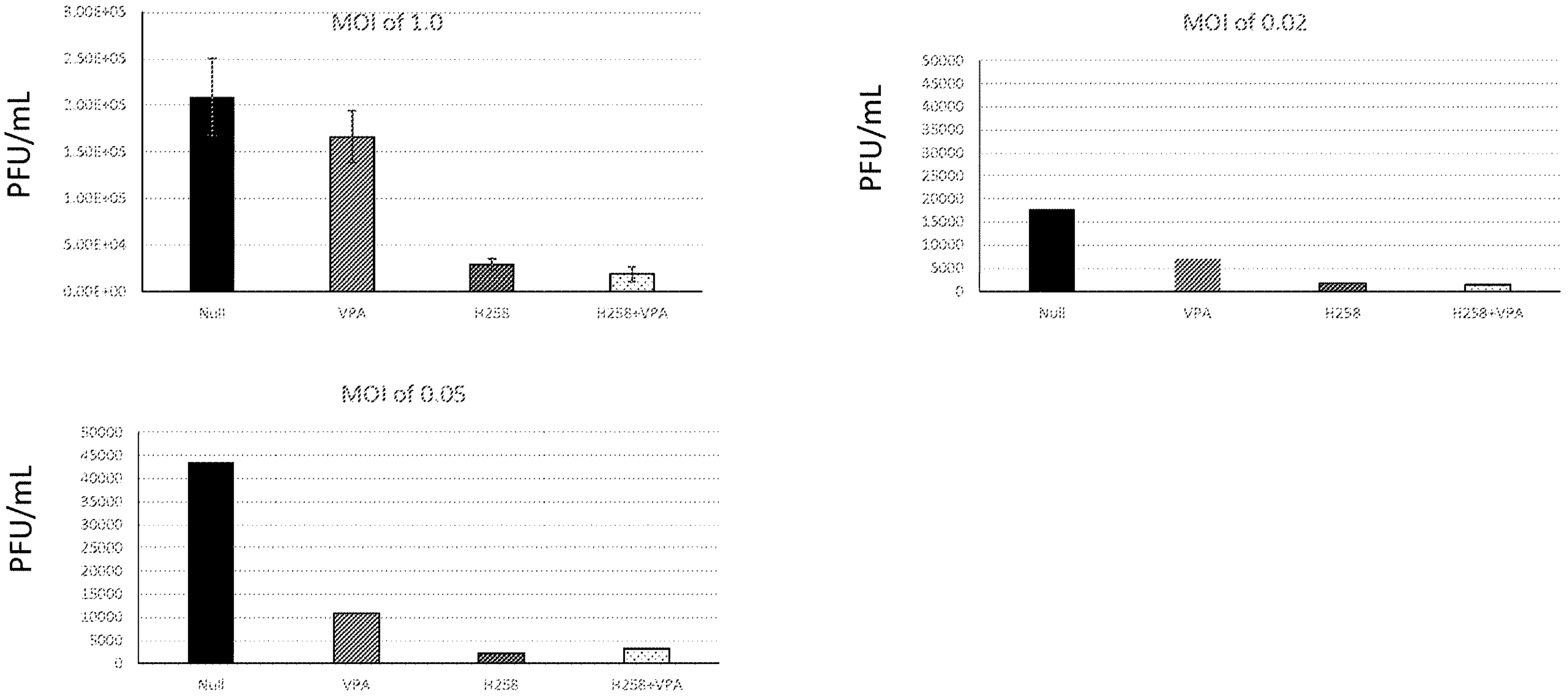

METHODS FOR TREATING A CYTOMEGALOVIRUS INFECTION

This application is a 35 U.S.C. 371 national stage entry of International Application No. PCT/US2015/062528, filed Nov. 24, 2015, which application claims the benefit of U.S. Provisional Application No. 62/084,954, filed Nov. 26, 2014, which applications are incorporated by reference herein in their entireties.

INTRODUCTION

Cytomegalovirus (CMV) is associated with widespread morbidity and mortality. Infection with CMV is common, and it has been estimated that between 50% and 85% of people in the United States have had a CMV infection by the time they are 40 years old. Although CMV infection generally does not produce symptoms in healthy adults, high-risk groups, including immunocompromised organ transplant recipients and HIV-infected individuals, are at risk of developing CMV-associated disease. CMV is a leading cause of birth defects.

LITERATURE

Baraldi et al. (2004) *Med. Res. Rev.* 24:475; Gravatt et al. (1994) *J. Med. Chem.* 37:4338; Nelson et al. (2007) *Mutation Res.* 623:24; Patel et al. (1991) *Invest. New Drugs* 9:53; U.S. Pat. No. 5,968,933; U.S. Patent Publication No. 2014/0212945; Kraut et al. (1991) *Invest. New Drugs* 9:95; Wong et al. (1994) *Biochem. Pharmacol.* 47:827; Mann et al. (2001) *J. Med. Chem.* 44:138; Smaill et al. (1998) *Anticancer Drug Des.* 13:857.

SUMMARY

The present disclosure provides a method for inhibiting cytomegalovirus (CMV) replication in a cell infected with CMV, the method comprising contacting the cell with a bisbenzimidazole compound. The present disclosure provides a method of treating a CMV infection in an individual, the method comprising administering to the individual an effective amount of a bisbenzimidazole compound.

The present disclosure provides method for inhibiting cytomegalovirus (CMV) replication in a cell infected with CMV, the method comprising contacting the cell with a bisbenzimidazole compound. In some cases, the bisbenzimidazole compound is 2'-(4-hydroxyphenyl)-5-(4-methyl-1-piperazinyl)-2,5'-bi-1H-benzimidazole trihydrochloride hydrate (Hoechst 33258). In some cases, the bisbenzimidazole compound is Hoechst 33342.

The present disclosure provides a method of treating a CMV infection in an individual, the method comprising administering to the individual an effective amount of a bisbenzimidazole compound. In some cases, the bisbenzimidazole compound is 2'-(4-hydroxyphenyl)-5-(4-methyl-1-piperazinyl)-2,5'-bi-1H-benzimidazole trihydrochloride hydrate (Hoechst 33258). In some cases, the bisbenzimidazole compound is Hoechst 33342. In some cases, the bisbenzimidazole compound is administered orally. In some cases, the bisbenzimidazole compound is administered intravenously. In some cases, the bisbenzimidazole compound is administered at a dose of from 5 $mg/m^2/day$ to 50 $mg/m^2/day$. In some cases, the individual is a human. In some cases, the method comprises administering at least a second therapeutic agent. In some cases, the second therapeutic agent is ganciclovir, foscarnet, cidofovir, maribavir, or valganciclovir. In some cases, the second therapeutic agent is an HDAC inhibitor. In some cases, the individual is an organ transplant recipient. In some cases, the individual is a bone marrow transplant recipient. In some cases, the individual does not have a CMV infection, and is a prospective organ transplant recipient. In some cases, the individual does not have a CMV infection, and is a prospective bone marrow transplant recipient. In some cases, the individual is a pregnant female. In some cases, the individual is a neonate.

The present disclosure provides a method of inhibiting cytomegalovirus replication in an organ or tissue, the method comprising contacting the organ or tissue in vitro or ex vivo with a bisbenzimidazole compound. In some cases, the bisbenzimidazole compound is 2'-(4-hydroxyphenyl)-5-(4-methyl-1-piperazinyl)-2,5'-bi-1H-benzimidazole trihydrochloride hydrate (Hoechst 33258). In some cases, the bisbenzimidazole compound is Hoechst 33342. In some cases, the organ or tissue is contacted in vitro or ex vivo with the bisbenzimidazole compound for a period of time of from about 15 minutes to about 48 hours, or more than 48 hours. In some cases, the organ or tissue is contacted in vitro or ex vivo with the bisbenzimidazole compound in a liquid medium.

The present disclosure provides a method of reducing the likelihood that a transplant recipient will become infected with cytomegalovirus from a donor organ or tissue, the method comprising: a) contacting the organ or tissue in vitro or ex vivo with a bisbenzimidazole compound, thereby producing a bisbenzimidazole compound-treated organ or tissue; and b) transplanting the bisbenzimidazole compound-treated organ or tissue into the transplant recipient. In some cases, the bisbenzimidazole compound is 2'-(4-hydroxyphenyl)-5-(4-methyl-1-piperazinyl)-2,5'-bi-1H-benzimidazole trihydrochloride hydrate (Hoechst 33258). In some cases, the bisbenzimidazole compound is Hoechst 33342. In some cases, the organ or tissue is contacted in vitro or ex vivo with the bisbenzimidazole compound for a period of time of from about 15 minutes to about 48 hours, or more than 48 hours. In some cases, the organ or tissue is contacted in vitro or ex vivo with the bisbenzimidazole compound in a liquid medium.

BRIEF DESCRIPTION OF THE DRAWINGS

FIG. 16 (left panel) provides a graph showing that BB33258 binds primarily to a specific tetranucleotide motif. FIG. 16 (right panel) provides a table showing the binding motif and comparing various sequences to the hCMV CRS sequence. Light grey in the top four rows indicates homology with HCMV CRS sequence. Dark grey in $2^{nd}$, $3^{rd}$, and $4^{th}$ rows indicates divergence from HCMV CRS sequence. Grey sequences in the bottom two rows are artificial controls and were chosen from representative literature. Bolded and underlined bases may indicate BB33258 binding sites according to both literature and these binding results. A hCMV CRS sequence (SEQ ID NO:1) is provided in the first row. A ΔhCMV sequence (SEQ ID NO:2) is provided in the second row. A rhCMV sequence (SEQ ID NO:3) is provided in the third row. A mCMV sequence (SEQ ID NO:4) is provided in the fourth row. A negative control sequence (SEQ ID NO:5) is provided in the fifth row. A positive control sequence (SEQ ID NO:6) is provided in the sixth row.

FIG. 21 provides a graph showing flow cytometry data on TB40E infected ARPE cell at 17 h and 20 h post infection. Data was analyzed as described in Teng et al. Cell 2012 (cited herein), the disclosure of which is incorporated by reference herein.

FIG. 22 provides a graph (left) showing the effect of drug on HCMV TB40E virus replication levels, and cell images showing virus detection (right). uM=μM.

FIG. 23 provides graphs showing Hoescht 33258 inhibits HCMV infection across a wide range of virus concentrations. All time points were taken at 10 days post-infection as described in Teng et al. Cell 2012 (cited herein), the disclosure of which is incorporated by references herein.

DEFINITIONS

Figure 1:
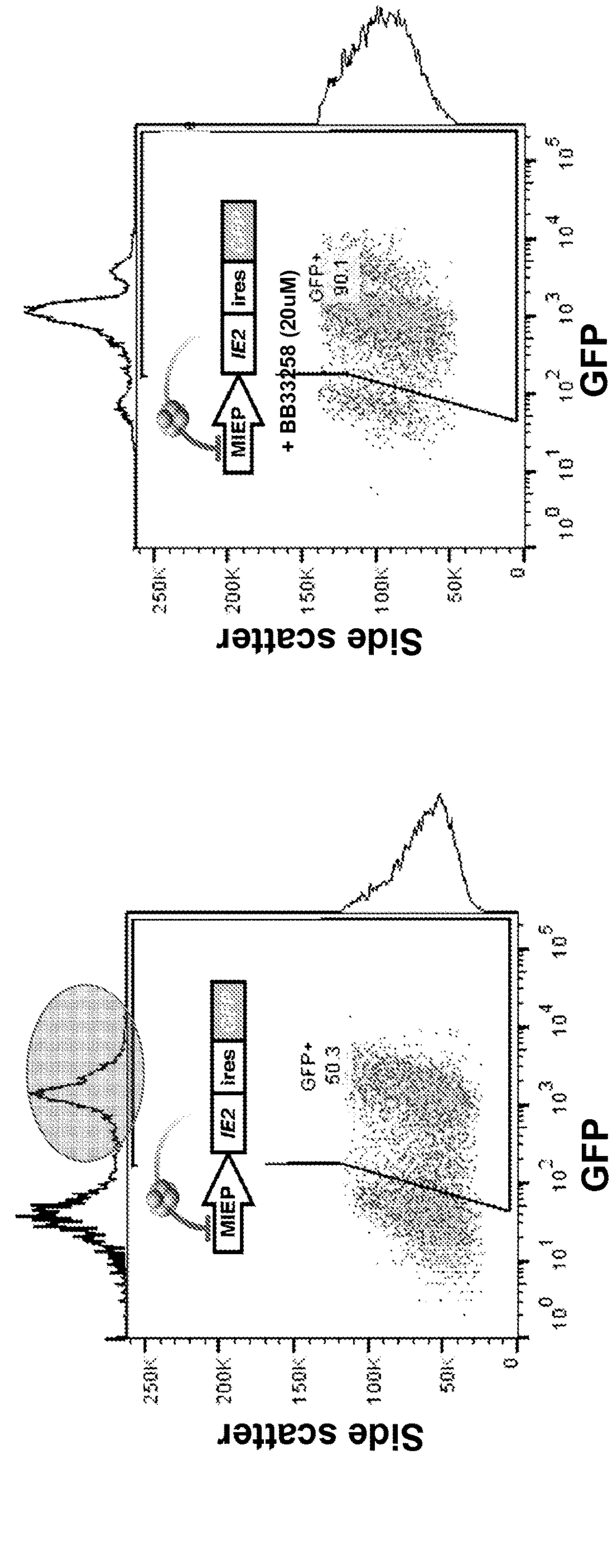
FIG. 1 depicts the effect of Hoechst 33258 on the IE2 negative feedback in ARPE-19 cells harboring the LM2ig (MIEP-IE2-IRES-GFP) construct.

The term "cytomegalovirus," also known as CMV, refers to a member of the herpesvirus family in any species, including human. CMV is also referred to as a Betaherpesviridae. CMV is a herpes virus that infects mononuclear cells and lymphocytes.

The term "human cytomegalovirus, or HCMV" indicates a member of the CMV family that infects humans. HCMV is a beta human herpesvirus with a genome size of 230 Kbp, coding more than 70 viral proteins. HCMV is also designated as human herpesvirus 5 (HHV-5). Mouse CMV (mCMV) indicates a member of the CMV family that infects mice. Rhesus monkey CMV (rhCMV) indicates a member of the CMV family that infects rhesus monkeys.

The terms "individual," "subject," "host," and "patient," used interchangeably herein, refer to a mammal, including, but not limited to, murines (rats, mice), non-human primates, humans, canines, felines, ungulates (e.g., equines, bovines, ovines, porcines, caprines), etc. In some cases, the individual is a human. In some cases, the individual is a non-human primate.

As used herein, the terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment," as used herein, covers any treatment of a disease in a mammal, particularly in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease.

A "therapeutically effective amount" or "efficacious amount" refers to the amount of a compound that, when administered to a mammal or other subject for treating a disease, is sufficient to effect such treatment for the disease. The "therapeutically effective amount" will vary depending on the compound or the cell, the disease and its severity and the age, weight, etc., of the subject to be treated.

The terms "co-administration" and "in combination with" include the administration of two or more therapeutic agents either simultaneously, concurrently or sequentially within no specific time limits. In one embodiment, the agents are present in the cell or in the subject's body at the same time or exert their biological or therapeutic effect at the same time. In one embodiment, the therapeutic agents are in the same composition or unit dosage form. In other embodiments, the therapeutic agents are in separate compositions or unit dosage forms. In certain embodiments, a first agent can be administered prior to (e.g., minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapeutic agent.

As used herein, a "pharmaceutical composition" is meant to encompass a composition suitable for administration to a subject, such as a mammal, especially a human. In general a "pharmaceutical composition" is sterile, and is free of contaminants that are capable of eliciting an undesirable response within the subject (e.g., the compound(s) in the pharmaceutical composition is pharmaceutical grade). Pharmaceutical compositions can be designed for administration to subjects or patients in need thereof via a number of different routes of administration including oral, buccal, rectal, parenteral, intraperitoneal, intradermal, intratracheal and the like. In some embodiments the composition is suitable for administration by a transdermal route, using a penetration enhancer other than dimethylsulfoxide (DMSO). In other embodiments, the pharmaceutical compositions are suitable for administration by a route other than transdermal administration. A pharmaceutical composition will in some embodiments include a subject compound and a pharmaceutically acceptable excipient. In some embodiments, a pharmaceutically acceptable excipient is other than DMSO.

As used herein, "pharmaceutically acceptable derivatives" of a compound of the invention include salts, esters, enol ethers, enol esters, acetals, ketals, orthoesters, hemiacetals, hemiketals, acids, bases, solvates, hydrates or prodrugs thereof. Such derivatives may be readily prepared by those of skill in this art using known methods for such derivatization. The compounds produced may be administered to animals or humans without substantial toxic effects and are either pharmaceutically active or are prodrugs.

A "pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a bisbenzimidazole compound" includes a plurality of such compounds and reference to "the composition" includes reference to one or more compositions and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides a method for inhibiting cytomegalovirus (CMV) replication in a cell infected with CMV, the method comprising contacting the cell with a bisbenzimidazole compound. The present disclosure provides a method of treating a CMV infection in an individual, the method comprising administering to the individual an effective amount of a bisbenzimidazole compound. The present disclosure provides a method of reactivating latent CMV in a cell in an individual, the method comprising administering to the individual an effective amount of a bisbenzimidazole compound.

In some cases, a suitable bisbenzimidazole compound specifically binds a 14-base pair cis-repression sequence in the CMV immediate early (IE) promoter, e.g., where the 14-base pair sequence is AT rich. Suitable bisbenzimidazole compounds include those described in U.S. Pat. No. 5,968,933. Suitable bisbenzimidazole compounds include those described in U.S. Patent Publication No. 2014/0212945.

In some cases, a suitable bisbenzimidazole compound has the following structure:

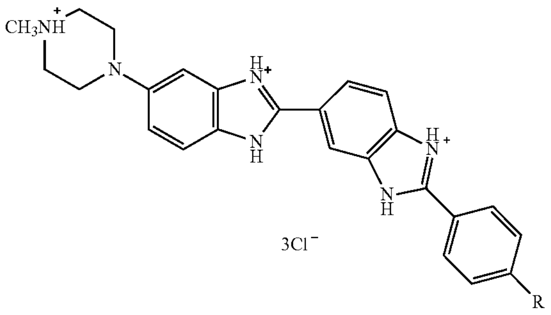

where R is OH, —O—$CH_2CH_3$, or $N(CH_3)_2$. In some cases, R is OH. In some cases, R is —O—$CH_2CH_3$.

In some cases, the compound is 2'-(4-hydroxyphenyl)-5-(4-methyl-1-piperazinyl)-2,5'-bi-1H-benzimidazole trihydrochloride hydrate, bisBenzimide. This compound is also known as Hoechst-33258. Hoechst-33258 has the structure:

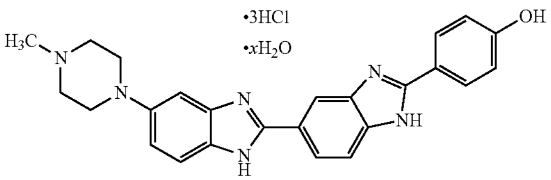 [SMILES: CN1CCN(c2ccc3[nH]c(-c4ccc5[nH]c(-c6ccc(O)cc6)nc5c4)nc3c2)CC1]

In some cases, the compound is (2'-[4-ethoxyphenyl]-5-[4-methyl-1-piperazinyl]-2,5'-bi-1H-benzimidazole trihydrochloride trihydrate). This compound is also known as Hoechst-33342. Hoechst-33342 has the following structure:

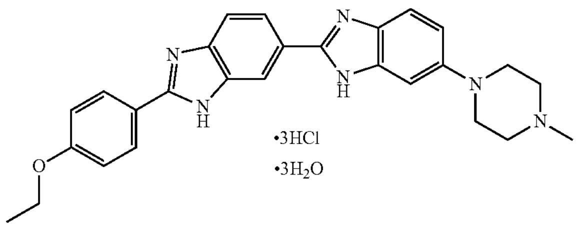

Hoechst 33342
MW 615.99

In some cases, a bisbenzimidazole compound (e.g., Hoechst 33258, Hoechst-33342, etc.) inhibits CMV replication by at least 10%, at least 20%, at least 30%, at least 40%, at least 50%, at least 60%, at least 70%, at least 80%, or at least 90%, compared to the level of CMV replication in a CMV-infected cell in the absence of the bisbenzimidazole compound. In some cases, a bisbenzimidazole compound (e.g., Hoechst 33258) inhibits human CMV replication by at least 10%, at least 20%, at least 30%, at least 40%, at least 50%, at least 60%, at least 70%, at least 80%, or at least 90%, compared to the level of human CMV replication in a human CMV-infected cell in the absence of the bisbenzimidazole compound.

In some cases, an effective amount of a bisbenzimidazole compound (e.g., Hoechst 33258, Hoechst-33342, etc.) is an amount that, when administered to an individual in need thereof in monotherapy or combination therapy in one or more doses, is effective to reduce CMV viral load in the individual by at least 10%, at least 20%, at least 30%, at least 40%, at least 50%, at least 60%, at least 70%, at least 80%, or at least 90%, compared to the viral load in the individual before treatment with the bisbenzimidazole compound, or in the absence of treatment with the bisbenzimidazole compound.

In some cases, an effective amount of a bisbenzimidazole compound (e.g., Hoechst 33258, Hoechst-33342, etc.) is an amount that, when administered to an individual in need thereof in monotherapy or combination therapy in one or more doses, is effective to reduce the number of CMV genome copies in the individual by at least 10%, at least 20%, at least 30%, at least 40%, at least 50%, at least 60%, at least 70%, at least 80%, or at least 90%, compared to the number of CMV genome copies in the individual before treatment with the bisbenzimidazole compound, or in the absence of treatment with the bisbenzimidazole compound.

In some cases, an effective amount of a bisbenzimidazole compound (e.g., Hoechst 33258, Hoechst-33342, etc.) is an amount that, when administered to an individual in need thereof in monotherapy or combination therapy in one or more doses, is effective to kill cells infected with CMV. For example, in some cases, an effective amount of a bisbenzimidazole compound (e.g., Hoechst 33258, Hoechst-33342, etc.) is an amount that, when administered to an individual in need thereof in monotherapy or combination therapy in one or more doses, is effective to kill at least 10%, at least 15%, at least 20%, at least 25%, at least 30%, at least 40%, at least 50%, at least 60%, at least 70%, or more than 70%, of the CMV-infected cells in the individual.

In some cases, a bisbenzimidazole compound (e.g., Hoechst 33258, Hoechst-33342, etc.) is administered prior to exposure of the individual to CMV. In some cases, a bisbenzimidazole compound (e.g., Hoechst 33258, Hoechst-33342, etc.) is administered after exposure of the individual to CMV. In some cases, a bisbenzimidazole compound (e.g., Hoechst 33258, Hoechst-33342, etc.) is administered to an individual who has been diagnosed as having a CMV infection.

In some cases, a bisbenzimidazole compound (e.g., Hoechst 33258, Hoechst-33342, etc.) is administered as monotherapy. In some cases, a bisbenzimidazole compound (e.g., Hoechst 33258, Hoechst-33342, etc.) is administered in combination therapy with one or more additional therapeutic agents.

In some cases, a bisbenzimidazole compound (e.g., Hoechst 33258, Hoechst-33342, etc.) is administered to an individual prior to exposure of the individual to CMV. In some cases, a bisbenzimidazole compound (e.g., Hoechst 33258, Hoechst-33342, etc.) is administered to an individual after exposure of the individual to CMV. In some cases, a bisbenzimidazole compound (e.g., Hoechst 33258, Hoechst-33342, etc.) is administered to an individual who has been diagnosed as having a CMV infection.

Formulations, Dosages, and Routes of Administration

In general, an active agent (e.g., a bisbenzimidazole compound (e.g., Hoechst 33258, Hoechst-33342, etc.) is prepared in a pharmaceutically acceptable composition(s) for delivery to a host. In the context of reducing CMV replication or treating a CMV infection, the terms "active agent," "drug," "agent," "therapeutic agent," and the like are used interchangeably herein to refer to an agent that is a a bisbenzimidazole compound (e.g., Hoechst 33258, Hoechst-33342, etc.) and that inhibits CMV replication.

Pharmaceutically acceptable carriers suitable for use with active agents (and optionally one or more additional therapeutic agents) may include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, and microparticles, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. A composition comprising an active agent (and optionally one or more additional therapeutic agent) may also be lyophilized using means well known in the art, for subsequent reconstitution and use according to the invention.

Formulations

An active agent is administered to an individual in need thereof in a formulation with a pharmaceutically acceptable excipient(s). A wide variety of pharmaceutically acceptable excipients is known in the art and need not be discussed in detail herein. Pharmaceutically acceptable excipients have been amply described in a variety of publications, including, for example, A. Gennaro (2000) "Remington: The Science and Practice of Pharmacy", 20th edition, Lippincott, Williams, & Wilkins; Pharmaceutical Dosage Forms and Drug Delivery Systems (1999) H. C. Ansel et al., eds 7$^{th}$ ed., Lippincott, Williams, & Wilkins; and Handbook of Pharmaceutical Excipients (2000) A. H. Kibbe et al., eds., 3$^{rd}$ ed. Amer. Pharmaceutical Assoc. For the purposes of the following description of formulations, "active agent" includes an active agent as described above, and optionally one or more additional therapeutic agent.

In pharmaceutical dosage forms, an active agent may be administered in the form of its pharmaceutically acceptable salts, or it may also be used alone or in appropriate association, as well as in combination, with other pharmaceutically active compounds. The following methods and excipients are merely exemplary and are in no way limiting.

In some embodiments, an active is formulated in an aqueous buffer. Suitable aqueous buffers include, but are not limited to, acetate, succinate, citrate, and phosphate buffers varying in strengths from about 5 mM to about 100 mM. In some embodiments, the aqueous buffer includes reagents that provide for an isotonic solution. Such reagents include, but are not limited to, sodium chloride; and sugars e.g., mannitol, dextrose, sucrose, and the like. In some embodiments, the aqueous buffer further includes a non-ionic surfactant such as polysorbate 20 or 80. Optionally the formulations may further include a preservative. Suitable preservatives include, but are not limited to, a benzyl alcohol, phenol, chlorobutanol, benzalkonium chloride, and the like. In many cases, the formulation is stored at about 4° C. Formulations may also be lyophilized, in which case they generally include cryoprotectants such as sucrose, trehalose, lactose, maltose, mannitol, and the like. Lyophilized formulations can be stored over extended periods of time, even at ambient temperatures.

For oral preparations, an active agent can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

An active agent can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The term "unit dosage form," as used herein, refers to physically discrete units suitable as unitary dosages for human and animal subjects, each unit containing a predetermined quantity of an active agent, calculated in an amount sufficient to produce the desired effect in association with a pharmaceutically acceptable diluent, carrier or vehicle. The specifications for a given active agent will depend in part on the particular compound employed and the effect to be achieved, and the pharmacodynamics associated with each compound in the host.

Suitable excipient vehicles are, for example, water, saline, dextrose, glycerol, ethanol, or the like, and combinations thereof. In addition, if desired, the vehicle may contain minor amounts of auxiliary substances such as wetting or emulsifying agents or pH buffering agents. Actual methods of preparing such dosage forms are known, or will be apparent, to those skilled in the art. See, e.g., Remington's Pharmaceutical Sciences, Mack Publishing Company, Easton, Pa., 17th edition, 1985. The composition or formulation to be administered will, in any event, contain a quantity of the agent adequate to achieve the desired state in the subject being treated.

Dosages

Although the dosage used will vary depending on the clinical goals to be achieved, a suitable dosage range of an active agent is one which provides up to about 1 mg to about 1000 mg, e.g., from about 1 mg to about 25 mg, from about 25 mg to about 50 mg, from about 50 mg to about 100 mg, from about 100 mg to about 200 mg, from about 200 mg to about 250 mg, from about 250 mg to about 500 mg, or from about 500 mg to about 1000 mg of an active agent can be administered in a single dose.

Suitable dosages include, e.g., from about 5 $mg/m^2/day$ to 50 $mg/m^2/day$, e.g., from 5 $mg/m^2/day$ to 7.5 $mg/m^2/day$, from 7.5 $mg/m^2/day$ to 10 $mg/m^2/day$, from 10 $mg/m^2/day$ to 20 $mg/m^2/day$, from 20 $mg/m^2/day$ to 30 $mg/m^2/day$, from 30 $mg/m^2/day$ to 40 $mg/m^2/day$, or from 40 $mg/m^2/day$ to 50 $mg/m^2/day$.

Those of skill will readily appreciate that dose levels can vary as a function of the specific compound, the severity of the symptoms and the susceptibility of the subject to side effects. Preferred dosages for a given compound are readily determinable by those of skill in the art by a variety of means.

In some embodiments, a single dose of an active agent is administered. In other embodiments, multiple doses of an active agent are administered. Where multiple doses are administered over a period of time, an active agent is administered twice daily (qid), daily (qd), every other day (qod), every third day, three times per week (tiw), or twice per week (biw) over a period of time. For example, an active agent is administered qid, qd, qod, tiw, or biw over a period of from one day to about 2 years or more. For example, an active agent is administered at any of the aforementioned frequencies for one week, two weeks, one month, two months, six months, one year, or two years, or more, depending on various factors.

Where two different active agents are administered, a first active agent and a second active agent can be administered in separate formulations. A first active agent and a second active agent can be administered substantially simultaneously, or within about 30 minutes, about 1 hour, about 2 hours, about 4 hours, about 8 hours, about 16 hours, about 24 hours, about 36 hours, about 72 hours, about 4 days, about 7 days, or about 2 weeks of one another.

Routes of Administration

An active agent is administered to an individual using any available method and route suitable for drug delivery, including in vivo and ex vivo methods, as well as systemic and localized routes of administration.

Conventional and pharmaceutically acceptable routes of administration include intranasal, intramuscular, intratracheal, transdermal, subcutaneous, intradermal, topical application, intravenous, vaginal, nasal, and other parenteral routes of administration. An active agent can also be delivered to the subject by enteral administration, e.g., oral administration.

Combination Therapy

In some cases, a method of the present disclosure for treating a CMV infection in an individual comprises administering to the individual, in combined effective amounts: a) a bisbenzimidazole compound (e.g., Hoechst 33258, Hoechst-33342, etc.); and b) at least a second therapeutic agent. Suitable second therapeutic agents include, but are not limited to, ganciclovir, foscarnet, cidofovir, maribavir, valganciclovir, and intravenous immunoglobulin (IVIG). Suitable second agents include, but are not limited to, histone deacetylase (HDAC) inhibitors. Suitable second agents include, but are not limited to, transcriptional transactivators.

Suitable transcriptional transactivators include, e.g., protein kinase C agonists; prostratin; TNF-alpha; 12-deoxyphorbol 13-phenylacetate (DPP); protein-based therapeutic agents that act through related cell-signaling pathways (e.g., the HSV-1 VP16 transactivator); and the like. In some cases, the transcriptional transactivator is prostratin. In some cases, the transcriptional transactivator is TNF-$\alpha$. In some cases, the transcriptional transactivator is a prostratin analog as described in U.S. Pat. No. 8,067,632.

HDAC inhibitors are known in the art, and any of a variety of HDAC inhibitors can be used. In some cases, the HDAC inhibitor inhibits all Class I HDACs, but does not substantially inhibit any Class II HDAC or any Class III HDAC. In some cases, the HDAC inhibitor specifically inhibits HDAC1 (and does not substantially inhibit other HDAC polypeptides, e.g., does not substantially inhibit HDAC 2, 3, 4, 5, 6, 7, 8, 9, or 10, or any Class III HDAC). In some cases, the HDAC inhibitor specifically inhibits HDAC2 (and does not substantially inhibit other HDAC polypeptides, e.g., does not substantially inhibit HDAC 1, 3, 4, 5, 6, 7, 8, 9, or 10, or any Class III HDAC). In some cases, the HDAC inhibitor inhibits both HDAC1 and HDAC2, but does not substantially inhibit other HDAC polypeptides, e.g., does not substantially inhibit HDAC 3, 4, 5, 6, 7, 8, 9, or 10, or any Class III HDAC.

Examples of HDAC inhibitors include trichostatin A (TSA) ((R,2E,4E)-7-(4-(dimethylamino)phenyl)-N-hydroxy-4,6-dimethyl-7-oxohepta-2,4-dienamide); suberoylanilide hydroxamic acid (SAHA); sulfonamides such as oxamflatin ((E)-N-hydroxy-5-(3-(phenylsulfonamido)phenyl)pent-2-en-4-ynamide); and belinostat (PXD101) ((E)-N-hydroxy-3-(4-(N-phenylsulfamoyl)phenypacrylamide). Other hydroxamic-acid-sulfonamide inhibitors of histone deacetylase are described in: Lavoie et al. (2001) Bioorg. Med. Chem. Lett. 11:2847-50; Bouchain et al. (2003) J. Med. Chem. 846:820-830; Bouchain et al. (2003) Curr. Med. Chem. 10:2359-2372; Marson et al. (2004) Bioorg. Med. Chem. Lett. 14:2477-2481; Finn et al. (2005) Hely. Chim. Acta 88:1630-1657; WO2002030879; WO2003082288; WO20050011661; WO2005108367; WO2006123121; WO2006017214; WO2006017215; and US2005/0234033. Other structural classes of histone deacetylase inhibitors include short chain fatty acids, cyclic peptides, and benzamides. Acharya et al. (2005) Mol. Pharmacol. 68:917-932.

In some cases, the HDAC inhibitor is a short-chain fatty acid, e.g., a butyrate or a phenylbutyrate. In some cases, the HDAC inhibitor is an epoxyketone-containing cyclic tetrapeptide, e.g. trapoxin. In some cases, the HDAC inhibitor is a non-epoxyketone-containing cyclic tetrapeptide. In some cases, the HDAC inhibitor is a hydroxamic acid, e.g., SAHA. In some cases, the HDAC inhibitor is a benzamide. In some cases, the HDAC inhibitor is valproate. In some cases, the HDAC inhibitor is TSA. In some cases, the HDAC inhibitor is PXD101.

Further examples of HDAC inhibitors include those disclosed in, e.g., Dokmanovic et al. (2007) Mol. Cancer. Res. 5:981; U.S. Pat. Nos. 7,642,275; 7,683,185; 7,732,475; 7,737,184; 7,741,494; 7,772,245; 7,795,304; 7,799,825; 7,803,800; 7,842,727; 7,842,835; U.S. Patent Publication No. 2010/0317739; U.S. Patent Publication No. 2010/0311794; U.S. Patent Publication No. 2010/0310500; U.S. Patent Publication No. 2010/0292320; and U.S. Patent Publication No. 2010/0291003. In some cases, a given HDAC inhibitor or class of HDAC inhibitors is specifically excluded.

Reducing CMV in Transplant Organs and Tissues

The present disclosure provides a method of inhibiting CMV replication in an organ or tissue, the method comprising contacting the organ or tissue in vitro or ex vivo with a bisbenzimidazole compound. In some cases, the bisbenzimidazole compound is 2'-(4-hydroxyphenyl)-5-(4-methyl-1-piperazinyl)-2,5'-bi-1H-benzimidazole trihydrochloride hydrate (Hoechst 33258). In some cases, the bisbenzimidazole compound is Hoechst 33342. The present disclosure provides a method of reducing the amount of CMV (e.g., reducing the number of genome copies of CMV) in an organ or tissue, the method comprising contacting the organ or tissue in vitro or ex vivo with a bisbenzimidazole compound. In some cases, the bisbenzimidazole compound is 2'-(4-hydroxyphenyl)-5-(4-methyl-1-piperazinyl)-2,5'-bi-1H-benzimidazole trihydrochloride hydrate (Hoechst 33258). In some cases, the bisbenzimidazole compound is Hoechst 33342. In some cases, the organ or tissue is autologous (the organ or tissue is obtained from a donor, where the donor is also the recipient of the organ or tissue). In some cases, the organ or tissue is allogeneic (the organ or tissue is obtained from a genetically different donor of the same species as the recipient). In some cases, the organ or tissue is xenogeneic (the organ or tissue is obtained from a different species from the recipient).

Organs and tissues suitable for use in a subject method include, but are not limited to, a kidney, a liver, a pancreas, a heart, a lung, skin, blood tissue (including whole blood; red blood cells; white blood cells; cord blood; and the like, where the blood tissue may comprise an isolated population of blood cells (buffy coat; red blood cells; platelets; lymphocytes; T cells; B cells; or some other population), or where the blood tissue comprises a mixed population of cells), small intestine, an endothelial tissue, a vascular tissue (e.g., a blood vessel), an eye, a stomach, a thymus, bone, bone marrow, cornea, a heart valve, an islet of Langerhans, or a tendon. As used herein, "organ" encompasses a whole organ or a part of an organ. As used herein, "tissue" encompasses a whole tissue or part of a tissue. As used herein, "tissue" encompasses a cell population.

In some cases, the organ or tissue is contacted in vitro or ex vivo with the bisbenzimidazole compound for a period of time of from about 15 minutes to about 48 hours, or more than 48 hours. For example, in some cases, the organ or tissue is contacted in vitro or ex vivo with the bisbenzimidazole compound for a period of time of from 15 minutes to 1 hour, from 1 hour to 2 hours, from 2 hours to 4 hours, from 4 hours to 8 hours, from 8 hours to 12 hours, from 12 hours to 24 hours, from 24 hours to 48 hours, or more than 48 hours.

In some cases, the organ or tissue is contacted in vitro or ex vivo with the bisbenzimidazole compound in an amount and for a period of time to reduce the CMV genome copies in the organ or tissue. In some cases, an effective amount of a bisbenzimidazole compound (e.g., Hoechst 33258, Hoechst-33342, etc.) is an amount that, when contacted with an organ or tissue, is effective to reduce the number of CMV genome copies in the organ or tissue by at least 10%, at least 20%, at least 30%, at least 40%, at least 50%, at least 60%, at least 70%, at least 80%, or at least 90%, compared to the number of CMV genome copies in the organ or tissue before contacting with the bisbenzimidazole compound, or in the absence of contacting with the bisbenzimidazole compound. In some cases, an effective amount of a bisbenzimidazole compound (e.g., Hoechst 33258, Hoechst-33342, etc.) is an amount that, when contacted with an organ or tissue for a period of time of from about 2 hours to 48 hours, is effective to reduce the number of CMV genome copies in the organ or tissue by at least 10%, at least 20%, at least 30%, at least 40%, at least 50%, at least 60%, at least 70%, at least 80%, or at least 90%, compared to the number of CMV genome copies in the organ or tissue before contacting with the bisbenzimidazole compound, or in the absence of contacting with the bisbenzimidazole compound.

In some cases, the organ or tissue is contacted in vitro or ex vivo with the bisbenzimidazole compound in a liquid medium. The liquid medium can comprise, in addition to the bisbenzimidazole compound, one or more of a buffer, a salt, a preservative, etc. In some cases, the liquid medium comprises, in addition to the bisbenzimidazole compound, one or both of an HDAC inhibitor, and a transcriptional transactivator.

The present disclosure provides a method of reducing the likelihood that a transplant recipient will become infected with cytomegalovirus from a donor organ, tissue, or cell population, the method comprising: a) contacting the organ or tissue in vitro or ex vivo with a bisbenzimidazole compound, thereby producing a bisbenzimidazole compound-treated organ or tissue; and b) transplanting the bisbenzimidazole compound-treated organ or tissue into the transplant recipient. In some cases, the bisbenzimidazole compound is 2'-(4-hydroxyphenyl)-5-(4-methyl-1-piperazinyl)-2,5'-bi-1H-benzimidazole trihydrochloride hydrate (Hoechst 33258). In some cases, the bisbenzimidazole compound is Hoechst 33342. In some cases, the organ or tissue is contacted in vitro or ex vivo with the bisbenzimidazole compound for a period of time of from about 15 minutes to about 48 hours, or more than 48 hours. For example, in some cases, the organ or tissue is contacted in vitro or ex vivo with the bisbenzimidazole compound for a period of time of from 15 minutes to 1 hour, from 1 hour to 2 hours, from 2 hours to 4 hours, from 4 hours to 8 hours, from 8 hours to 12 hours, from 12 hours to 24 hours, from 24 hours to 48 hours, or more than 48 hours. In some cases, the organ or tissue is contacted in vitro or ex vivo with the bisbenzimidazole compound in a liquid medium. The liquid medium can comprise, in addition to the bisbenzimidazole compound, one or more of a buffer, a salt, a preservative, etc. In some cases, the liquid medium comprises, in addition to the bisbenzimidazole compound, one or both of an HDAC inhibitor, and a transcriptional transactivator. In some cases, the organ or tissue is autologous (the organ or tissue is obtained from a donor, where the donor is also the recipient of the organ or tissue). In some cases, the organ or tissue is allogeneic (the organ or tissue is obtained from a genetically different donor of the same species as the recipient). In some cases, the organ or tissue is xenogeneic (the organ or tissue is obtained from a different species from the recipient).

Subjects Suitable for Treatment

Subjects suitable for treatment with a method of the present disclosure for treating a CMV infection include individuals who have been diagnosed as having a CMV infection. Subjects suitable for treatment with a method of the present disclosure for treating a CMV infection include individuals who have not been diagnosed as having a CMV infection. In some cases, the individual does not have a CMV infection, but is at greater risk than the general population of contracting a CMV infection.

In some cases, the individual has a CMV infection, and also has an immunodeficiency virus (e.g., human immunodeficiency virus; HIV) infection. In some cases, the individual does not have an immunodeficiency virus (e.g., human immunodeficiency virus; HIV) infection.

In some cases, the individual is an organ transplant recipient. In some cases, the individual is a liver transplant recipient. In some cases, the individual is a kidney transplant recipient. In some cases, the individual is a liver transplant recipient. In some cases, the individual is a bone marrow transplant recipient. In some cases, the individual is a lung transplant recipient.

In some cases, the individual does not have a CMV infection; and is a prospective organ transplant recipient. In some cases, the individual does not have a CMV infection; and is a prospective liver transplant recipient. In some cases, the individual does not have a CMV infection; and is a prospective kidney transplant recipient. In some cases, the individual does not have a CMV infection; and is a prospective bone marrow transplant recipient. In some cases, the individual does not have a CMV infection; and is a prospective lung transplant recipient.

In some cases, the individual is a pregnant female, e.g., a pregnant human female. In some cases, the individual is a neonate, e.g., a human neonate. In some cases, the individual is from 1 hour old to 4 weeks old, e.g., from 1 hour to 4 hours, from 4 hours to 8 hours, from 8 hours to 12 hours, from 12 hours to 1 day, from 1 day to 1 week, or from 1 week to 4 weeks, old. In some cases, the individual is from 4 weeks old to 6 months old.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal (ly); s.c., subcutaneous(ly); and the like.

Example 1: Effects of Bisbenzimidazole Compounds on CMV Replication

Materials and Methods

Unless otherwise noted, all references to CMV are to human CMV (hCMV).

Cell-Culture Conditions and Drug Perturbations

MRCS fibroblasts and life-extended human foreskin fibroblasts (HFFs) (Bresnahan and Shenk, 2000) were maintained in Dulbecco's Modified Eagle's Medium (DMEM) supplemented with 10% fetal bovine serum (FBS) and 50 U/ml penicillin-streptomycin at 37° C. and 5% $CO_2$ in a humidified incubator. ARPE-19 cells were maintained in a 1:1 mixture of DMEM/F-12 (Mediatech Inc.) with 10% FBS (HyClone) and 50 U/ml Penicillin-Streptomycin (Mediatech Inc.). Cells were treated with a final concentration of 1 mM valproic acid (VPA) (Calbiochem™), resuspended in dimethylsulfoxide, for approximately 24 hours before imaging. Cells were treated with a final concentration of 400 nM TSA (Sigma-Aldrich) resuspended in dimethylsulfoxide, for 20-24 hours, a final concentration of 10 ng/mL TNF-α (Sigma-Aldrich) resuspended in phosphate-buffered saline (PBS), or a final concentration of 1 mM VPA (Calbiochem) for approximately 24 hours before imaging.

Reactivation of latent CMV in N-Tera2 cells was conducted as previously described in (Meier, 2001).

Cloning of Reporter LM2ig and Flow Cytometry

Standard lentiviral cloning was used to create minimal major immediate early (MIE) circuits (Dull et al., 1998). The minimal MIEP-IE2-GFP and MIEP-GFP circuits are driven by a full-length ~2.5 kb MIE promoter-enhancer (MIEP) that spans the sequence from the MIEP modulator at the 5' edge to the junction of immediate early (IE) exons 1 and 2. The MIEP was polymerase chain reaction (PCR)-cloned from AD169 into pLEIGW in place of the EF1a promoter. This full-length MIEP drives an IE2-IRES-GFP or mCherry-IRES-GFP cassette. IE2 was cloned from pRSV-IE86 (a gift from Jay Nelson). ARPE-19 cells were infected and fluorescence-activated cell sorter (FACS) sorted for green fluorescent protein (GFP) fluorescence to create stably expressing cell lines. Cells were treated with Trichostatin-A (TSA) for 17 hours, and GFP expression was quantified by flow cytometry. Live cells were gated by forward-versus-side scattering on a FacsCalibur™ cytometer (BD Biosciences) and mean fluorescence intensity recorded. At least 20,000 live cells were recorded for each experiment and data was analyzed in FlowJo™ (Treestar Inc.).

Figure 7:
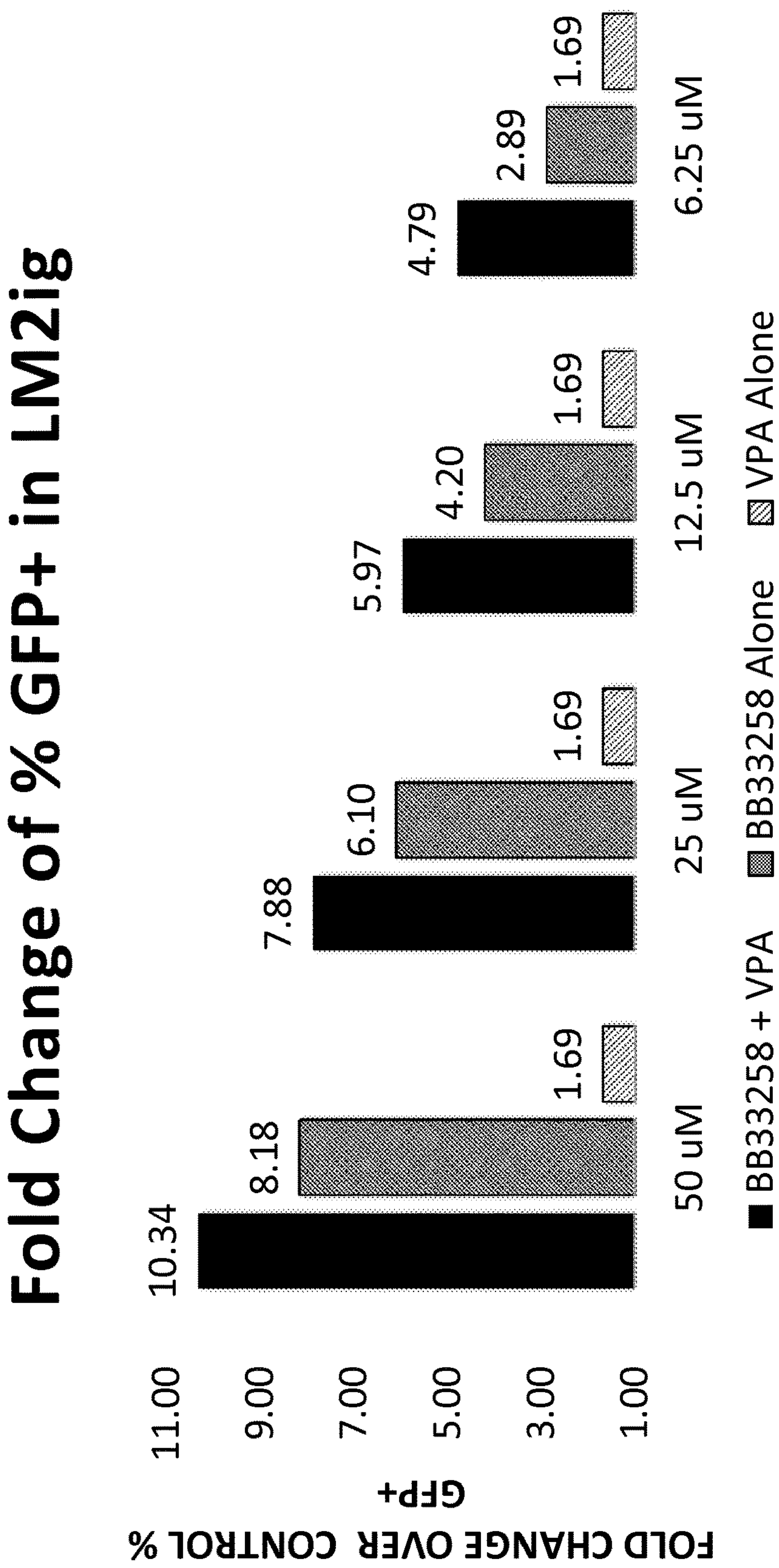
FIG. 7 depicts the effect of Hoechst 33258, alone or with VPA, on the percent of GFP-positive cells after treatment of ARPE-19 cells harboring the LM2ig construct.
Figure 13:
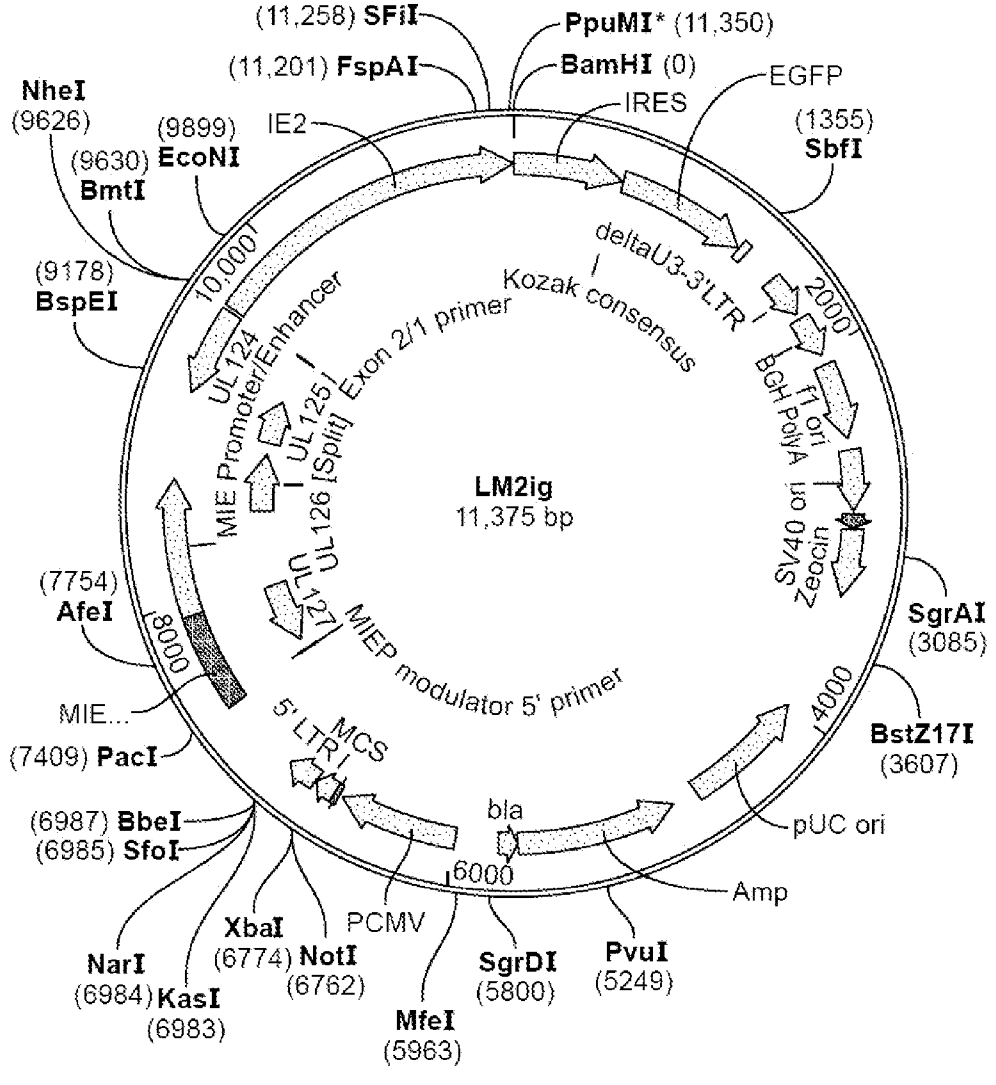
FIG. 13 provides a map of vector LM2ig.

See WO 2014/127148 for descriptions of MIEP-IE2-reporter constructs. For example, LM2ig construct is depicted in FIG. 7 of WO 2014/127148. A map of LM2ig is provided in FIG. 13.

Cloning of Recombinant Viruses

The CMV immediate early2-yellow fluorescent protein (IE2-YFP) virus and CMV Δcrs IE2-YFP have been previously described (Teng et al., 2012). Briefly, the parent CMV IE2-YFP virus were constructed in the CMV AD169 background (Bankier et al., 1991) by inserting EYFP (Clontech) to the 3' end of IE2 exon 5 in the parent AD169 bacterial artificial chromosome (BAC) (Moorman et al., 2008; Yu et al., 2002). The CMV Δcrs IE2-YFP virus was constructed by BAC 'recombineering' (Warming et al., 2005) of the CMV IE2-YFP virus as previously described (Cuevas-Bennett and Shenk, 2008). The integrity of all BAC recombinant viruses was verified by: (i) restriction digest using HindIII and EcoRI to verify banding patterns (New England BioLabs), (ii) direct sequencing of the recombineered locus and 1000 bp in each direction, (iii) replication kinetics of the resulting virus, and (iv) EYFP or EGFP expression. To propagate and purify virus, BAC DNA was electroporated (Yu et al., 2002) into MRCS cells (American Type Culture Collection) using a GenePulser Xcell Electroporation System (Bio-Rad). Upon infection reaching 100% viral cytopathic effect or 100% GFP, the culture supernatant was collected and filtered with a 0.2 μm filter (Corning Inc.). For the CMV Δcrs IE2-YFP virus, low titers required concentration by ultracentrifugation: cells were disrupted by sonication to release virions, and supernatant was then filtered by a 0.45 μm filter and ultracentrifuged in a 'sorbitol cushion' (20% D-sorbitol, 50 mM Tris-HCl, pH 7.2, 1 mM $MgCl_2$ in $dH_2O$) in an SW 41 Ti rotor (Beckman Coulter, Inc.) at 25,000 rpm at 18° C. Viral stocks were titered by $TCID_{50}$ and converted to PFU/ml (Nevels et al., 2004).

Quantitative Western Blot Analysis

Cell monolayers were rinsed in PBS buffer, and cells from each well were scraped into 50 μl A of RIPA buffer and stored at −80° C. For analysis, samples were thawed and quantitated for total protein content using a modified Lowry assay (BioRad DC protein assay kit). Equivalent amounts of total protein (10 μg) were added to appropriate volumes of 4× sample loading buffer (50 mM Tris-HCl pH 6.8, 2% sodium docecyl sulfate (SDS), 10% glycerol, 1% beta-mercaptoethanol, 12.5 mM EDTA, and 0.02% bromophenol blue) and heated at 95° C. for 5 minutes. Protein samples were loaded and separated on precast SDS polyacrylamide gel electrophoresis (PAGE) 10% or 7.5% bisacrylamide gels (BioRad). Protein transfer and blot preparation were handled as previously described (Bolovan-Fritts et al., 2004). For detection of protein bands, primary mouse monoclonal antibody against a shared epitope present in IE1 and IE2 at 1:100 (MAB810, Millipore). Beta tubulin was used as a normalization marker, and detected by a primary rabbit anti-beta tubulin antibody (926-42211, LiCor) used at a dilution of 1:2000. The secondary antibody for IE2 detection used was a donkey anti-mouse conjugated to IR dye 800CW (926-32212, LiCor) at a dilution of 1:20,000. The secondary detection antibody for beta-tubulin was a donkey anti-rabbit IR dye 680RD (926-68073, LiCor) at a dilution of 1:20,000. Detection was carried out according to manufacturer's protocols. Blots were scanned using a LiCor Odyssey Infrared Imaging system and software analysis for quantitation.

Viral Replication Kinetics

MRCS cells were seeded into cell culture plates and maintained for 1 to 2 days until cells reached confluency at ~$5\times10^4$ cells per well. The monolayers were then infected with recombinant virus human CMV IE2-YFP or CMV-GFP as a control. HCMV IE2-YFP was used as the control virus for replication kinetics with the Δcrs IE2-YFP recombinant virus. Cells were infected at a multiplicity of infection (MOI) of 1, 0.2, or 0.1, as indicated. Inoculum was prepared using virus stocks diluted in culture media, and adsorbed onto cells in a volume of 200 μl for one hour at 37° C. in a humidified $CO_2$ incubator. Inoculum was then removed and replaced with one mL of fresh media. The amount of infectious virus to prepare inoculum was based on plaque assay titrations (Bolovan-Fritts and Wiedeman, 2001) of virus stocks and is shown as time point 0 in each figure. For each time point three separate sample wells were collected. Infectious cell-free virus was collected by harvesting medium from infected culture wells at indicated time points and stored at −80° C. To measure replication, samples were thawed and prepared as a 10-fold serial dilution series in culture media, then analyzed by $TCID_{50}$. The results were then converted to plaque-forming units per ml (PFU/ml). Error ranges were calculated using standard deviation.

Murine CMV (MCMV) replication kinetics were performed in BALB/c mice using the Smith strain of MCMV as previously described (Orr et al., 2010) and on NIH 3T3 cells using same methods as for HCMV. Rhesus CMV (RhCMV) viral replication kinetics were performed on rhesus fibroblast cells as described in (Lilja et al., 2008).

Results

FIG. 1 shows that IE2 negative feedback, in a minimal synthetic circuit setting, can be disrupted with Hoechst 33258 (also referred to as "BB33258"). ARPE-19 cells stably transduced with a MIEP-IE2-IRES-GFP construct (LM2ig) were subjected to FACS. FIG. 1, left panel, shows control data (cells cultured in medium without Hoechst 33258). FIG. 1, right panel, shows data from cells cultured in medium with Hoechst 33258. As shown in FIG. 1, right panel, Hoechst 33258 increased production of IE2, which in turn reduced cell viability.

Figure 2:
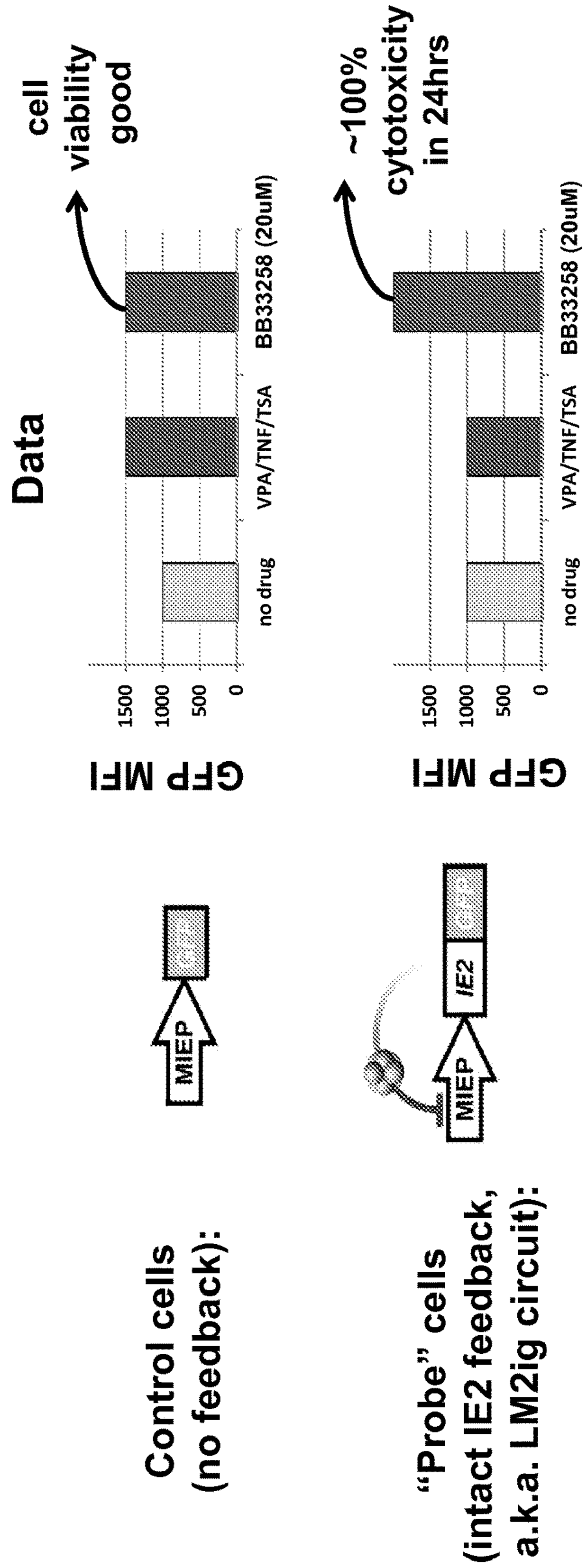
FIG. 2 depicts the effect of Hoechst 33258 on the IE2 negative feedback in ARPE-19 cells harboring the LM2ig construct, compared with the effect of valproic acid, tumor necrosis factor, and trichostatin A.

FIG. 2 shows that Hoechst 33258 increased production of IE2, as measured by GFP expression (expressed as GFP mean fluorescence intensity; GFP-MFI) in ARPE-19 cells stably transduced with LM2ig (MIEP-IE2-IRES-GFP construct), and reduced cell viability. Cells transfected with a control construct (MIEP-GFP) lacking IE2-encoding sequences expressed GFP, but were not killed. Valproic acid (VPA), trichostatin A (TSA), and tumor necrosis factor (TNF) also increased IE2 expression, but were not cytotoxic.

Figure 3:
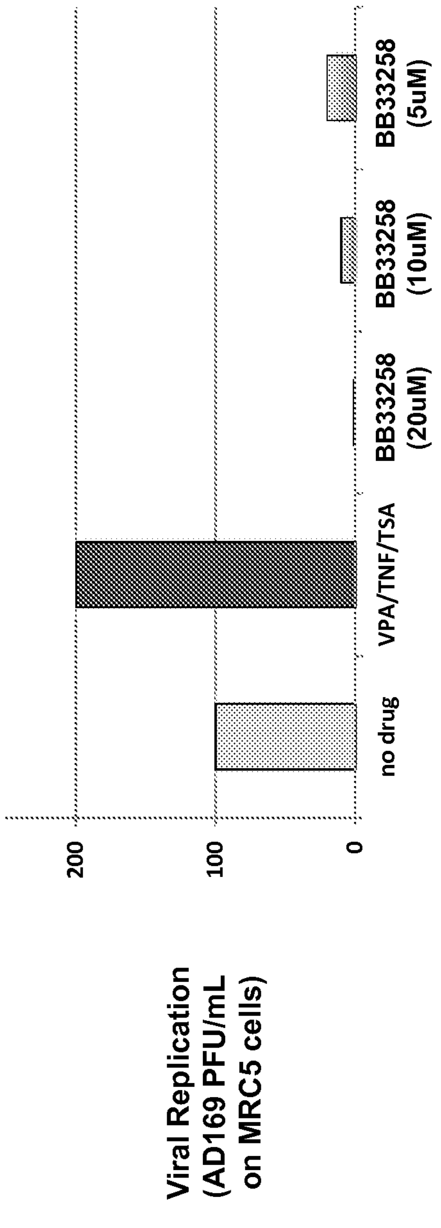
FIG. 3 depicts the effect of Hoechst 33258 on human CMV (hCMV) viral replication in MRCS cells (strain AD169).

FIG. 3 shows the effect of Hoechst 33258 on human CMV replication in MRCS cells. MRCS cells were infected with CMV AD169 (a laboratory strain of HCMV; GenBank X17403) in the absence ("no drug"), or in the presence of: i) VPAor TNF or TSA ("VPA/TNF/TSA"); ii) 20 μM Hoechst 33258 ("BB33258"); iii) 10 μM Hoechst 33258; or iv) 5 μM Hoechst 33258. The data are expressed in plaque-forming units (PFU)/ml. As shown in FIG. 3, Hoechst 33258, but not VPA/TNF/TSA, inhibited HCMV viral replication.

Figure 4:
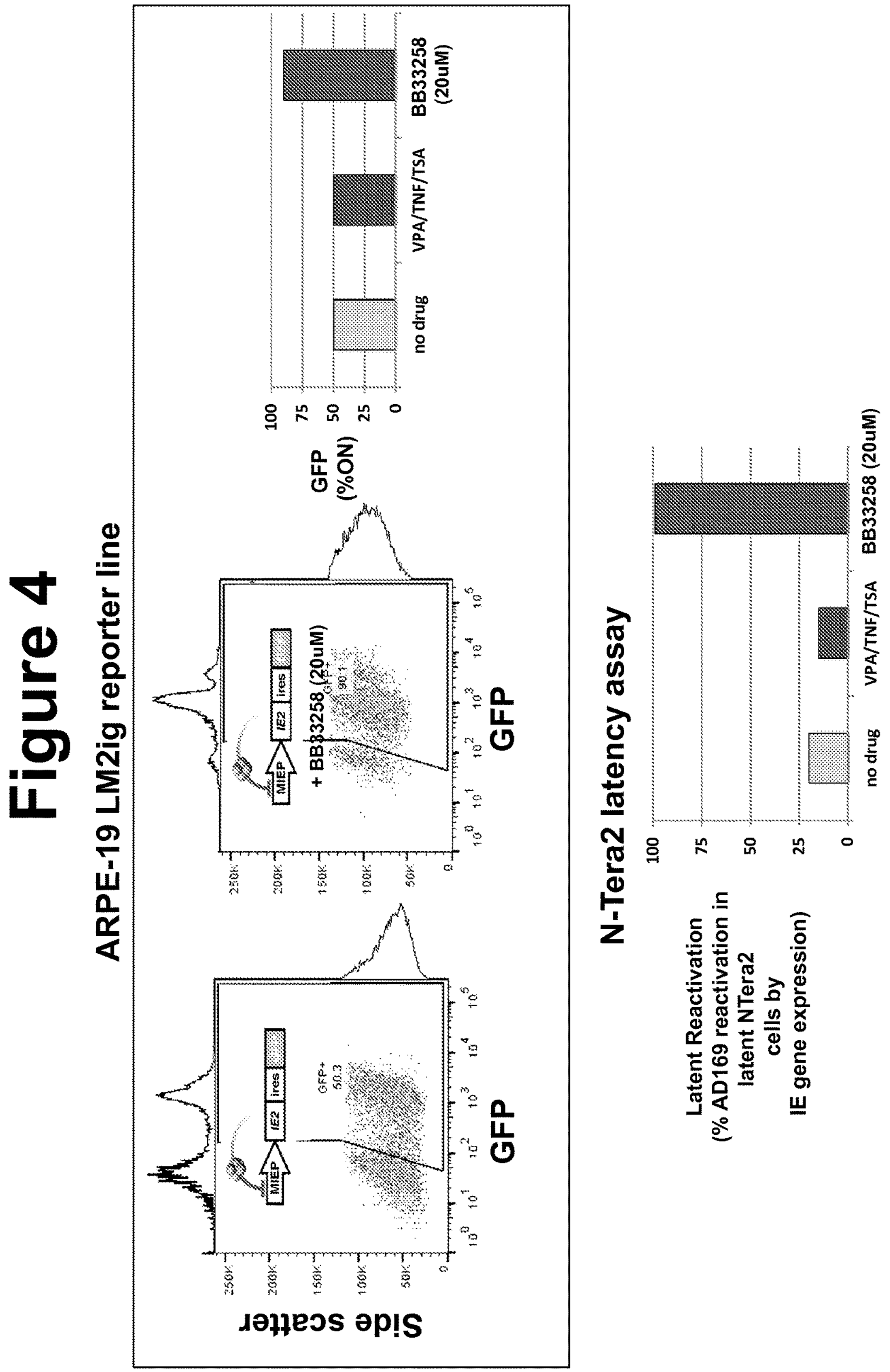
FIG. 4 depicts the effect of Hoechst 33258 on quiescent major immediate early promoter (MIEP)-driven expression in a reporter cell line, and on latent CMV.

FIG. 4 shows that Hoechst 33258 activates quiescent MIEP-driven expression in a reporter cell line, and reactivates latent CMV. ARPE-19 cells harboring the LM2ig construct were treated with 20 μM Hoechst 33258; the cells were then analyzed with FACS. As shown in FIG. 4, upper panel, Hoechst 33258, but not VPA, TNF, or TSA, activated quiescent MIEP-driven expression. As shown in FIG. 4, lower panel, Hoechst 33258, but not VPA, TNF, or TSA, reactivated latent CMV in the N-Tera2 latency assay.

Figure 5:
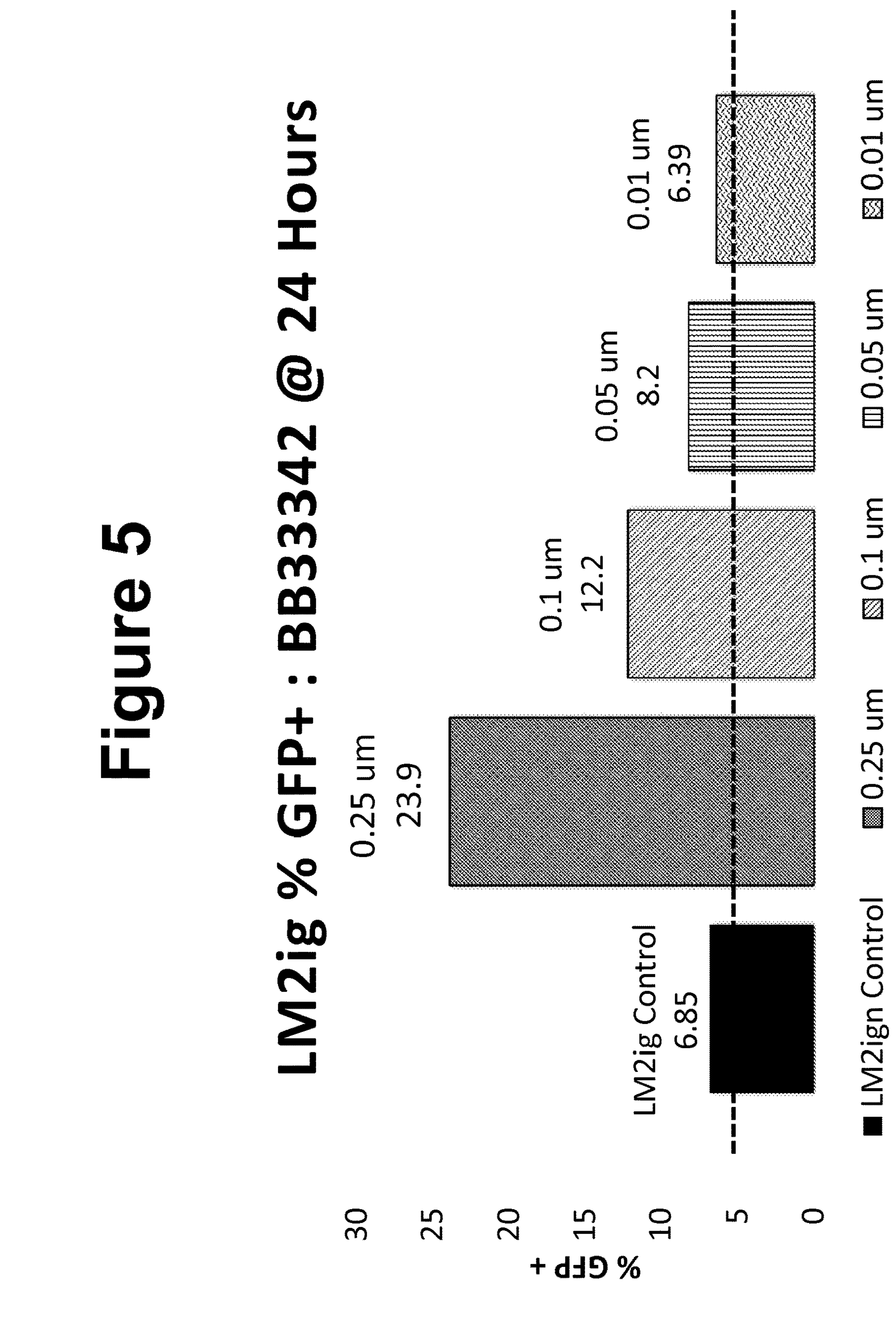
FIG. 5 depicts the effect of Hoechst 33342 on the percent of green fluorescent protein (GFP)-positive cells after treatment, for 24 hours, of ARPE-19 cells harboring the LM2ig construct.

FIG. 5 shows the effect of Hoechst 33342 (also referred to as "BB33342") on expression of GFP in MRCS cells transfected with the LM2ig construct. As shown in FIG. 5, the percent GFP-positive cells increased after 24 hours when cells were cultured in medium containing 0.25 μM Hoechst 33342.

Figure 6:
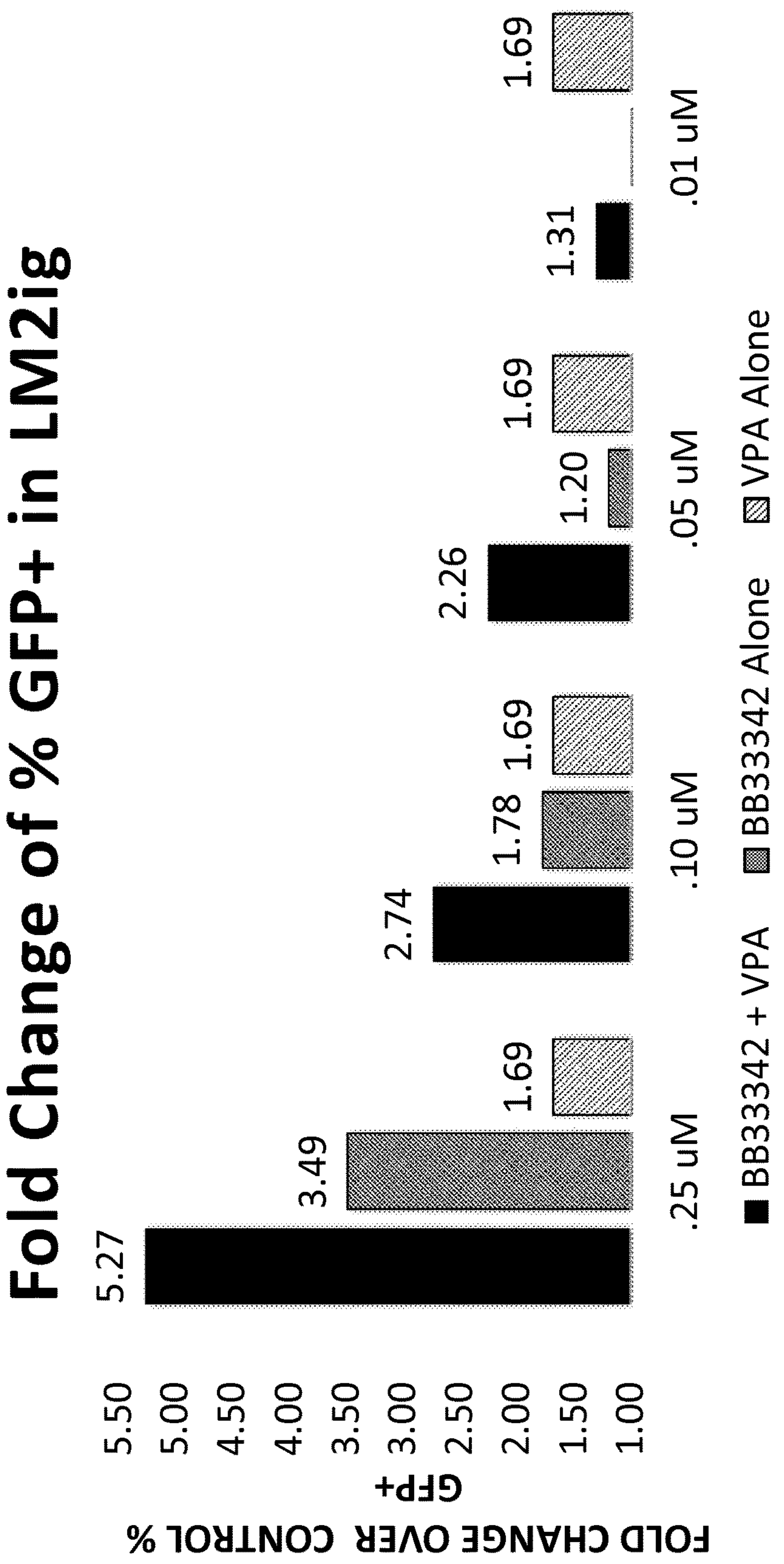
FIG. 6 depicts the effect of Hoechst 33342, alone or with valproic acid (VPA) on the percent of GFP-positive cells after treatment of ARPE-19 cells harboring the LM2ig construct.

FIG. 6 shows the effect of Hoechst 33342, with or without VPA, on GFP expression in MRCS cells harboring the LM2ig construct. As shown in FIG. 6, VPA alone induced a modest (1.69-fold) increase in the number of GFP-positive cells at all concentrations of VPA (concentrations of VPA used were as described in Teng et al. (2012). Cell 151, 1569-1580); Hoechst 33342 alone, at a concentration of 0.25 μM, induced a 3.49-fold increase in the number of GFP-positive cells; and the combination of 0.25 μM Hoechst 33342 and VPA (concentrations of VPA used were as described in Teng et al. (2012). Cell 151, 1569-1580) induced a 5.27-fold increase in the number of GFP-positive cells.

FIG. 7 shows the effect of a combination of Hoechst 33258 and VPA on expression of GFP in ARPE-19 cells harboring the LM2ig construct. As shown in FIG. 7, Hoechst 33258 alone induced an increase in the number of GFP-positive cells; VPA alone induced an increase in the number of GFP-positive cells at all concentrations of VPA; and the combination of Hoechst 33258 and VPA induced a greater increase in the number of GFP-positive cells, compared to either agent alone.

Figure 8:
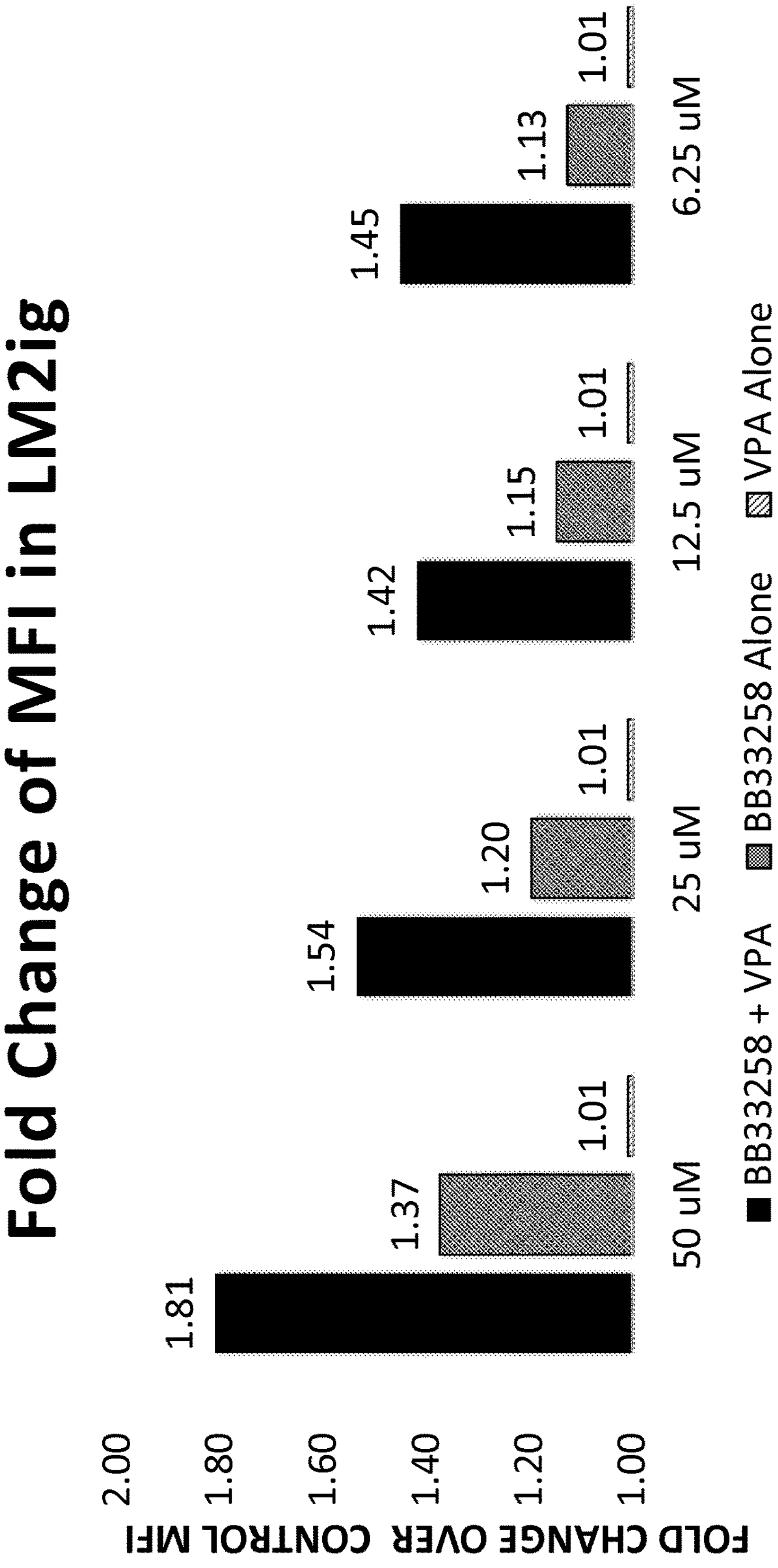
FIG. 8 depicts the effect on mean fluorescence intensity (MFI) of Hoechst 33258, alone or with VPA, after treatment of ARPE-19 cells harboring the LM2ig construct.

FIG. 8 shows the effect of Hoechst 33258, with or without VPA, on mean fluorescence intensity (MFI) in ARPE-19 cells harboring the LM2ig construct. As shown in FIG. 8, VPA alone did not substantially increase MFI; Hoechst 33258 alone increased MFI; and the combination of Hoechst 33258 and VPA resulted in a further increase in MFI, compared to Hoechst 33258 alone.

Breaking the IE2 circuit with Hoechst 33258 correlates with significantly reduced HCMV replication. Breaking the IE2 circuit with Hoechst 33258 correlates with reactivation of latent HCMV. Hoechst 33258 strongly reactivates the LM2ig minimal circuit after 24 hours; addition of VPA enhances this effect. Hoechst 33342 strongly reactivates the LM2ig minimal circuit; the addition of VPA enhances this effect. Hoechst 33342 alone does not break the minimal LM2ig circuit after 24 hours; however, addition of VPA may allow Hoechst 33342 to break this circuit.

The data indicated that 24-28 hour exposure to bisbenzimidazole compounds (Hoechst 33258 and Hoechst 33342) breaks the IE2 negative feedback circuit and that long-term (e.g., 8-10 days) exposure breaks the circuit and reactivates the promoter from an off (i.e. silenced) state corresponding to CMV latency. The data also indicated that increases in MFI are correlated with increases in cell death, indicating that increased IE2 levels are responsible for cell death. Quantitative Western blot data indicated that IE2 levels increase with increasing Hoechst 33258 exposure, in agreement with the GFP data.

Figure 9:
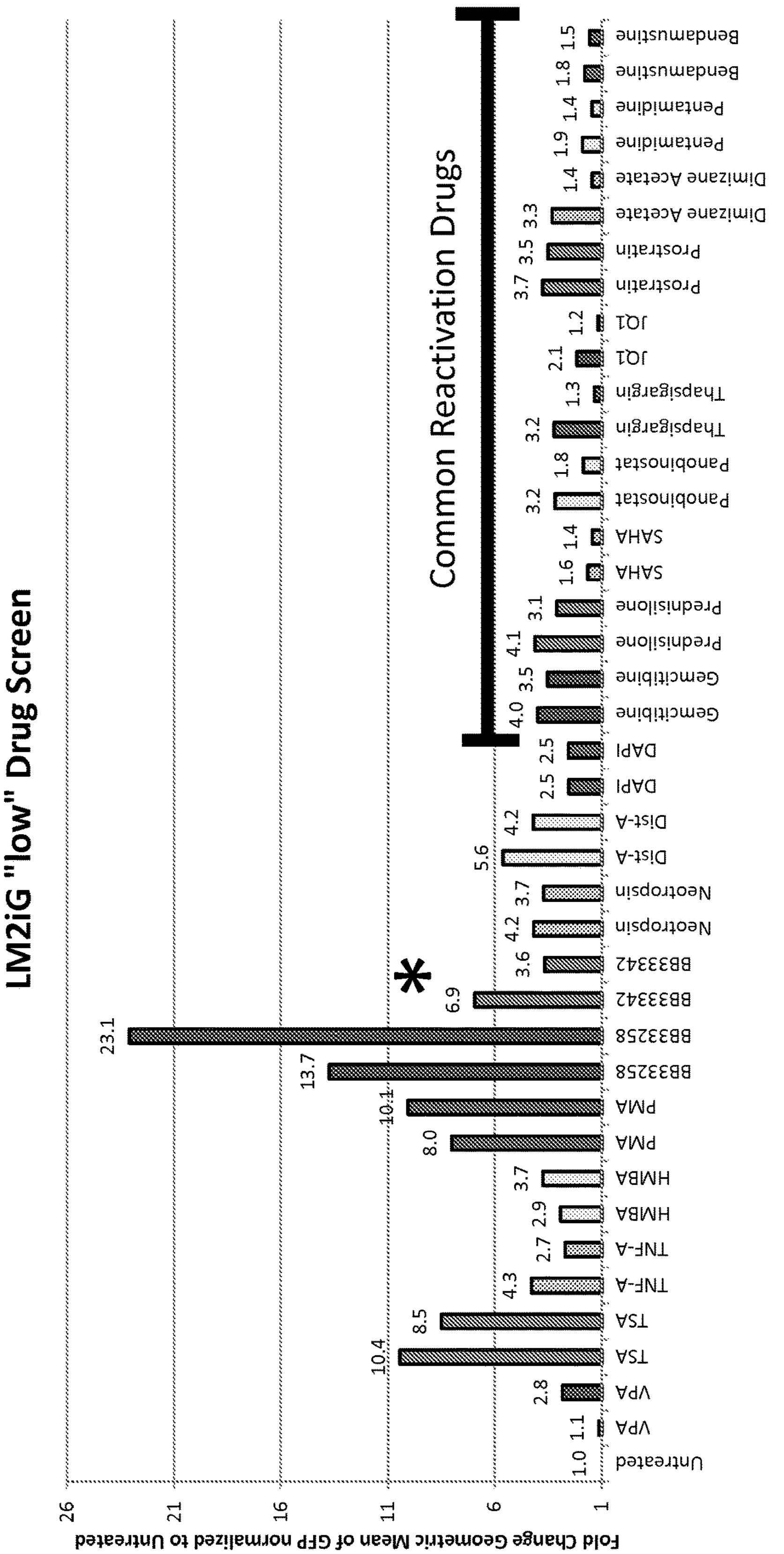
FIG. 9 depicts the effect of various compounds on the geometric mean of GFP in LM2ig "low" cells.

Using a LM2ig "low" drug screen, it was found that bisbenzimidazole compounds Hoechst 33258 and Hoechst 33342 specifically break the IE2 negative feedback. LM2ig "low" cells (~0% GFP positive before induction) were treated with agents in duplicate for an induction period of 4 days. During this induction period, the cell culture medium was not changed; images were taken every day for 4 days. On the final day, high throughput flow cytometry was carried out on FACS IntelliCyt. Agents tested were: Hoechst 33258, Hoechst 33342, VPA, TSA, TNF-α, hexamethylene bisacetamide (HMBA), phorbol myristate acetate (PMA), neotroposin, distamycin, DAPI, gemcitabine, prednisolone, suberanilohydroxamic acid (SAHA), (2E)-N-hydroxy-3-[4-({[2-(2-methyl-1H-indol-3-yl)ethyl]amino}methyl)phenyl] acrylamide (panobinostat), thapsigargin, JQ1, prostratin, dimizane acetate, pentamidine, or bendamustine. The data are shown in FIG. 9.

Figure 10:
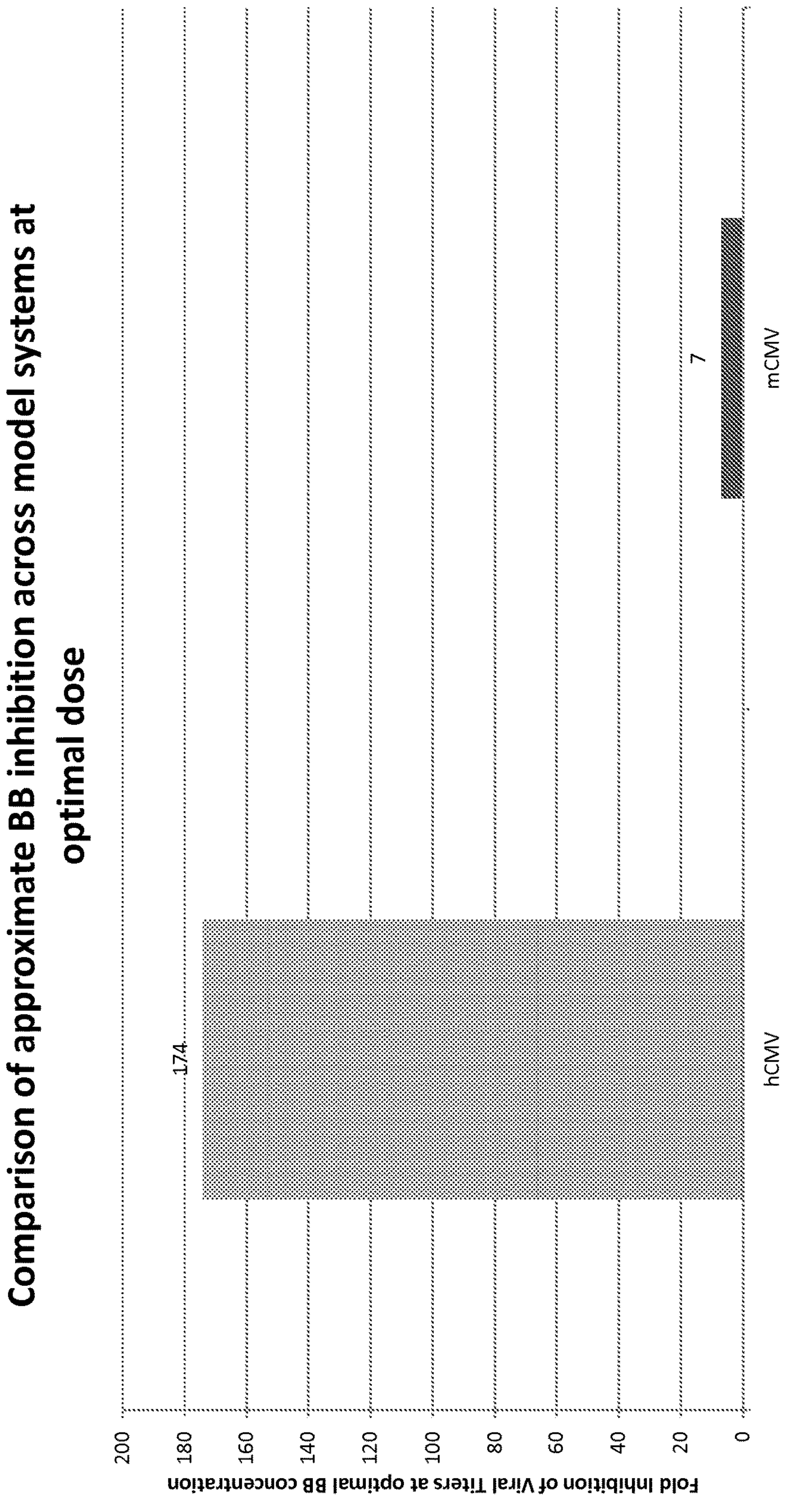
FIG. 10 depicts the effect of Hoechst 33258 on murine CMV (mCMV) replication and on hCMV replication.
Figure 11:
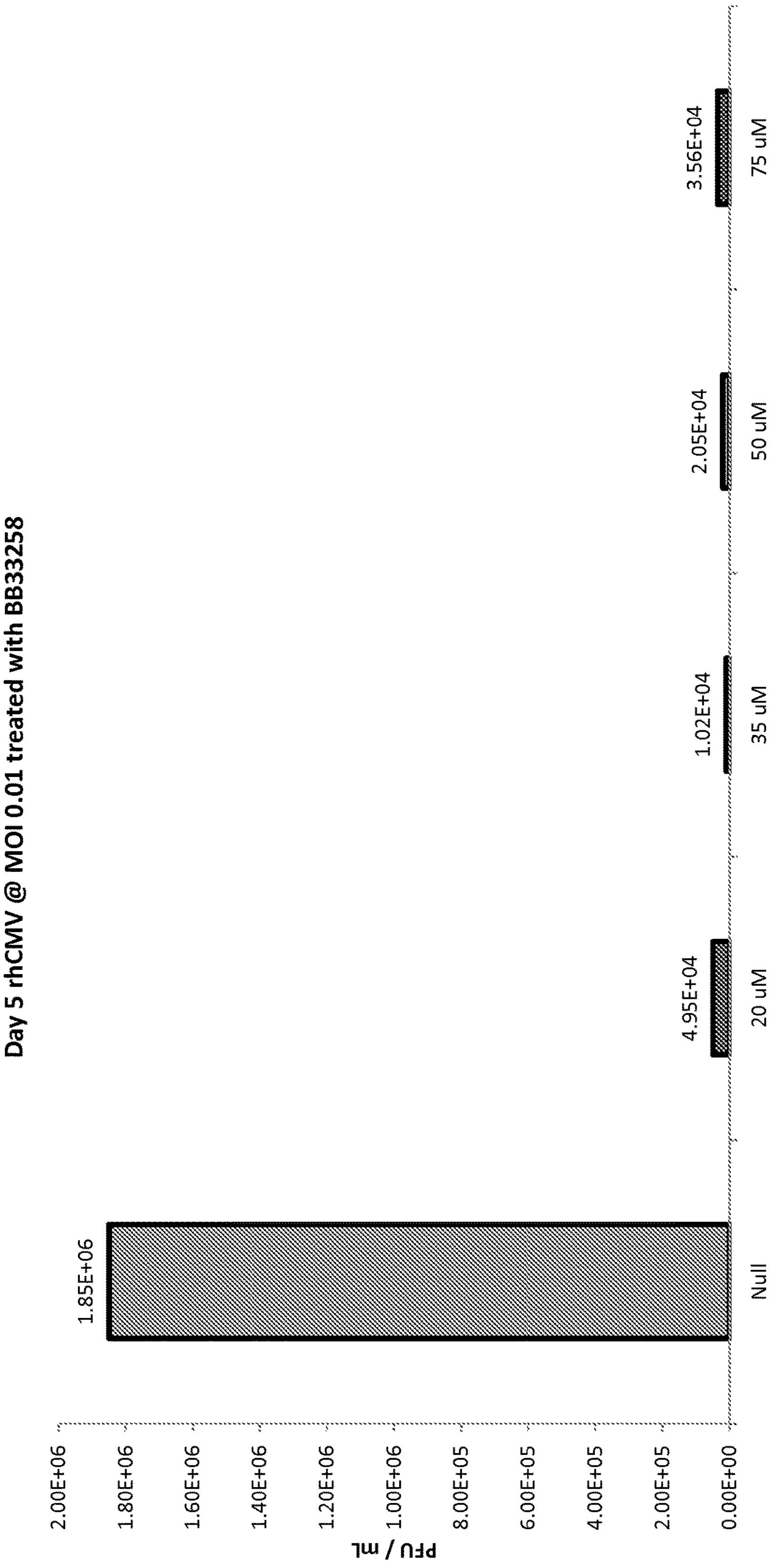
FIG. 11 depicts the effect of Hoechst 33258 on rhesus monkey CMV (rhCMV) replication.
Figure 12:
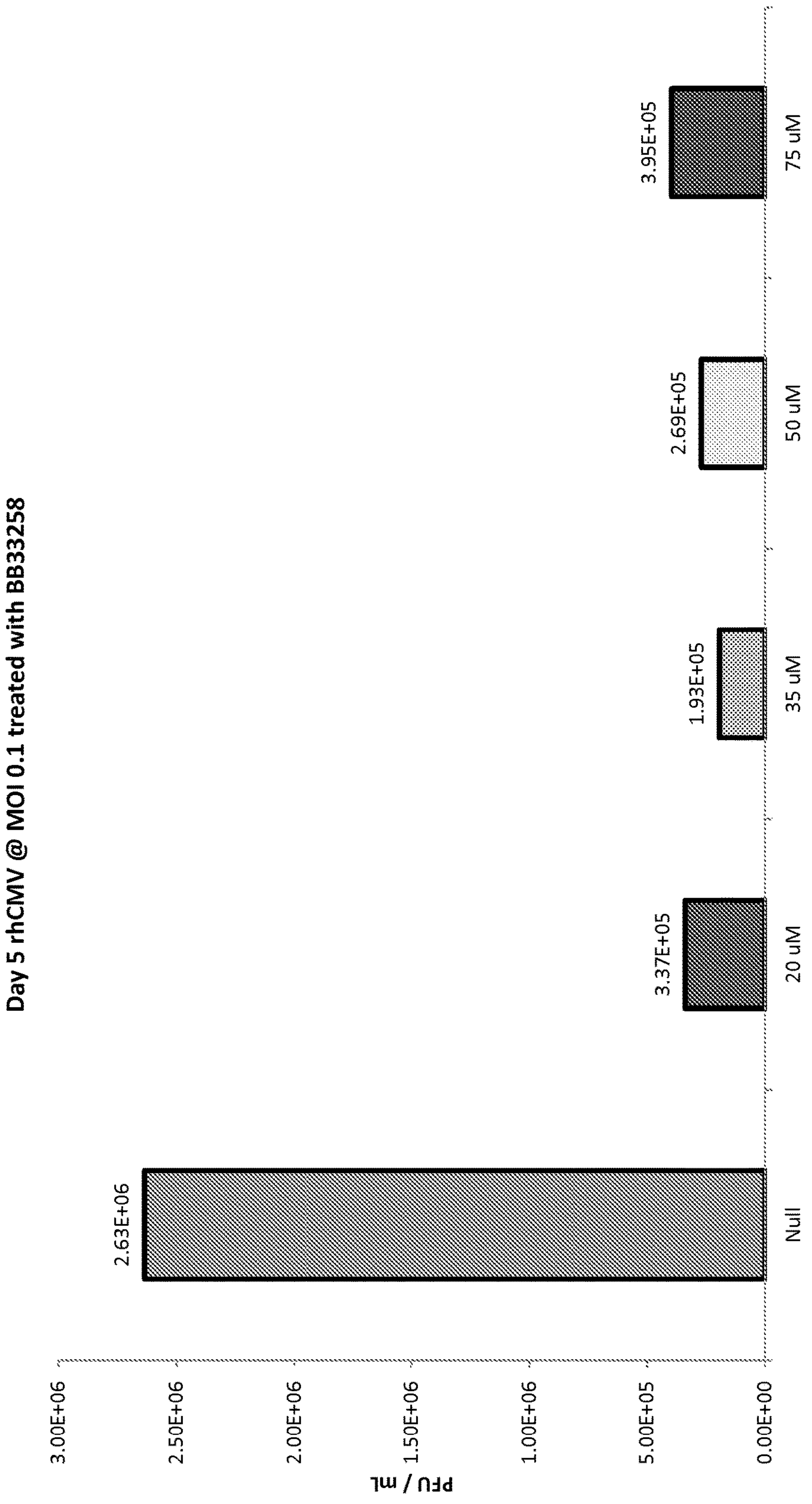
FIG. 12 depicts the effect of Hoechst 33258 on rhCMV replication at various multiplicities of infection, and after multiple rounds of replication.

The effect of bisbenzimidazole compound Hoechst 33258 on human CVM (hCMV), mouse CMV (mCMV) and rhesus monkey CMV (rhCMV) was tested. It was found that Hoechst 33258 reduces mCMV replication ~5-fold in mice. In contrast, as shown in FIG. 10, Hoechst 33258 reduced hCMV replication by more than 100 fold. As shown in FIG. 11, Hoechst 33258 inhibited rhCMV replication to an extent similar to Hoechst 33258 inhibition of hCMV replication. As shown in FIG. 12, the inhibitory effect of Hoechst 33258 remains both at high MOI and also after multiple rounds of replication. Microscopy supported the viral titer data, indicating inhibition of rhCMV. DIC imaging showed reduced cytopathic effect (CPE) and plaque formation in Hoechst 33258-treated, rhCMV-infected cells. The data indicated that rhCMV recapitulates the viral replication inhibition observed with hCMV.

A comparison of the CRS sequence (IE2 binding site) of hCMV, rhCMV, and mCMV shows that hCMV and rhCMV CRS sequences share 93% sequence similarity, rhCMV and mCMV CRS sequences share 40% sequence similarity, and hCMV and mCMV CRS sequences share 40% sequence similarity. Alignments are provided below:

```
                   (SEQ ID NO: 7)
 hCMV CRS: TCGTTTAGTGAACCG

                   (SEQ ID NO: 8)
rhCMV CRS: TCGTTTAGGGAACCG
                   *

                   (SEQ ID NO: 7)
 hCMV CRS: TCGTTTAGTGAACCG

                   (SEQ ID NO: 9)
 mCMV CRS: CCAGCGTCGGTACCG
           * ******* *

                   (SEQ ID NO: 8)
rhCMV CRS: TCGTTTAGGGAACCG

                   (SEQ ID NO: 9)
 mCMV CRS: CCAGCGTCGGTACCG
           * ******  *
```

Example 2: bisBenzimide Binding Assay

Materials and Methods

Figure 14:
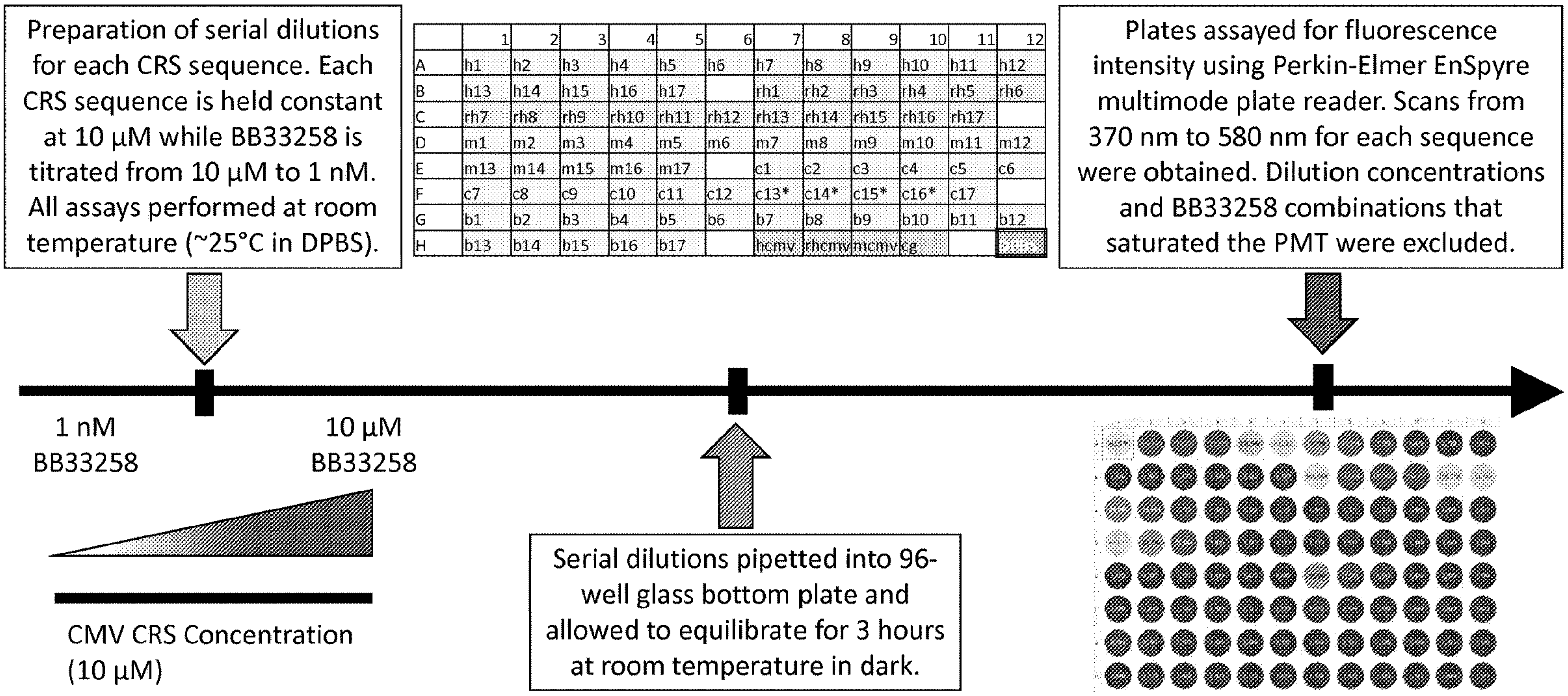
FIG. 14 depicts generally the steps of a bisBenzimide binding assay protocol according to Example 4.

A bisBenzimide binding assay protocol was performed as shown in FIG. 14. Serial dilutions for each CRS sequence were prepared. Each CRS sequence was held constant at 10 μM while BB33258 was titrated from 10 μM to 1 nM. All assays were performed at room temperature (~25° C. in DPBS). Serial dilutions were pipetted into 96-well glass bottom plate and allowed to equilibrate for 3 hours at room temperature in the dark. Plates were then assayed for fluorescence intensity using Perkin-Elmer EnSpyre multimode plate reader. Scans from 370 nm to 580 nm for each sequence were obtained. Dilution concentrations and BB33258 combinations that saturated the PMT were excluded.

Results

Figure 15:
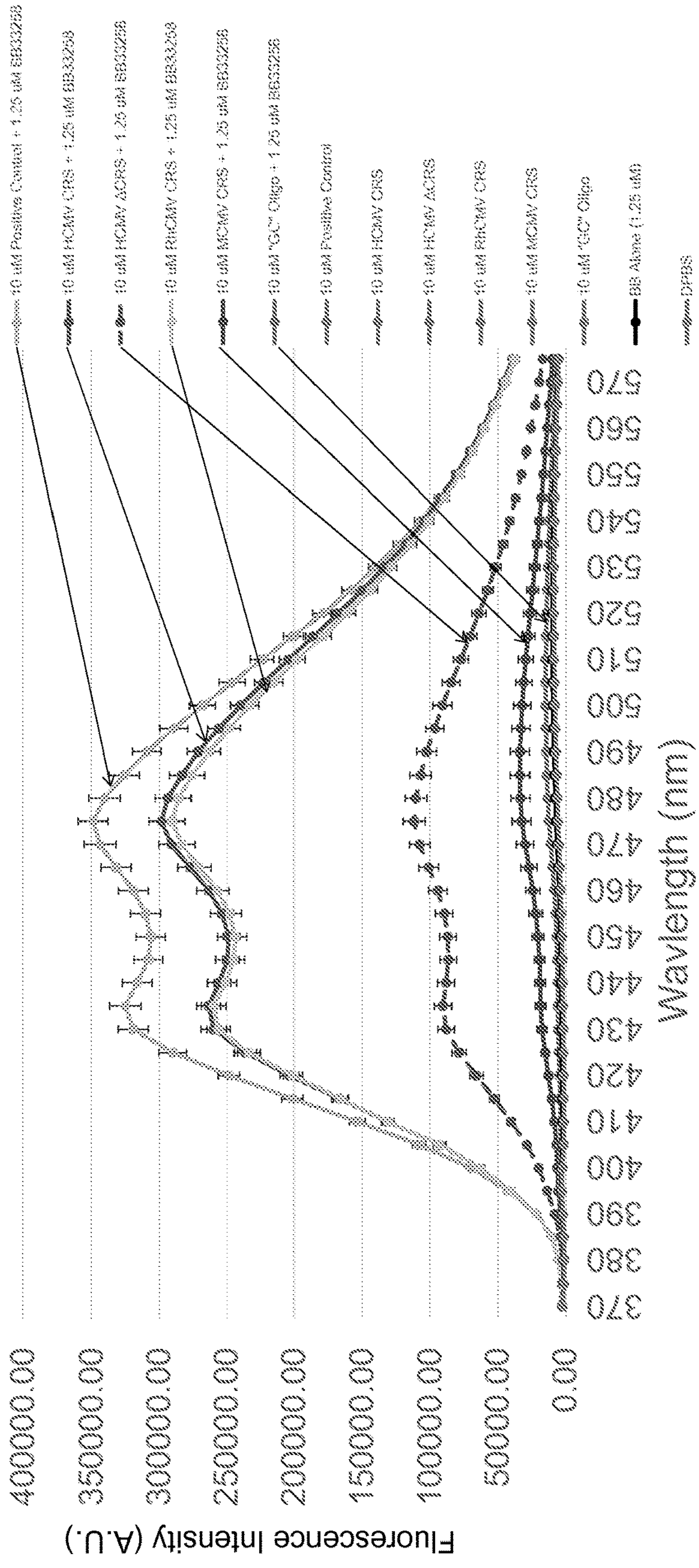
FIG. 15 provides a graph showing bisBenzimide 33258 promoter specificity. uM=μM.
Figure 17:
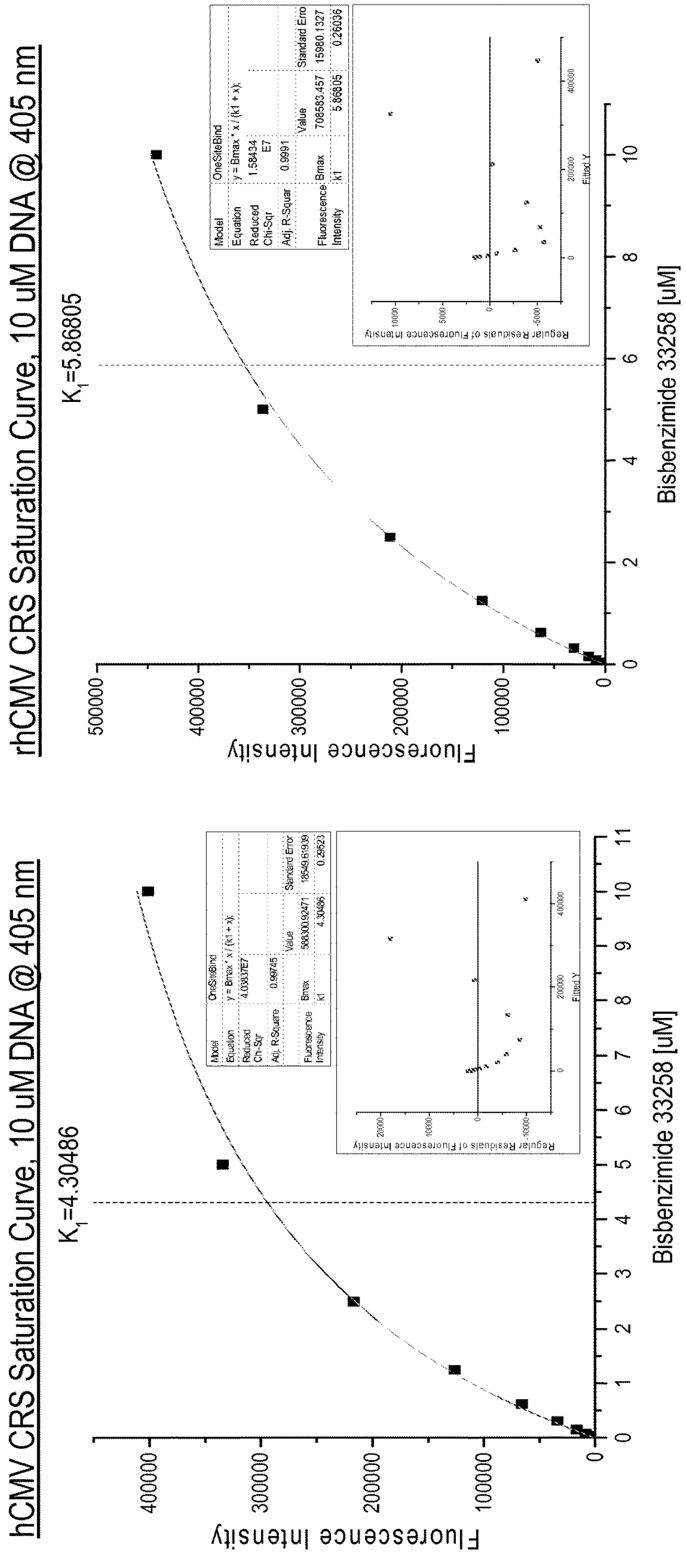
FIG. 17 provides bisBenzimide 33258 saturation curves for hCMV CRS and rhCMV CRS sequences.
Figure 18:
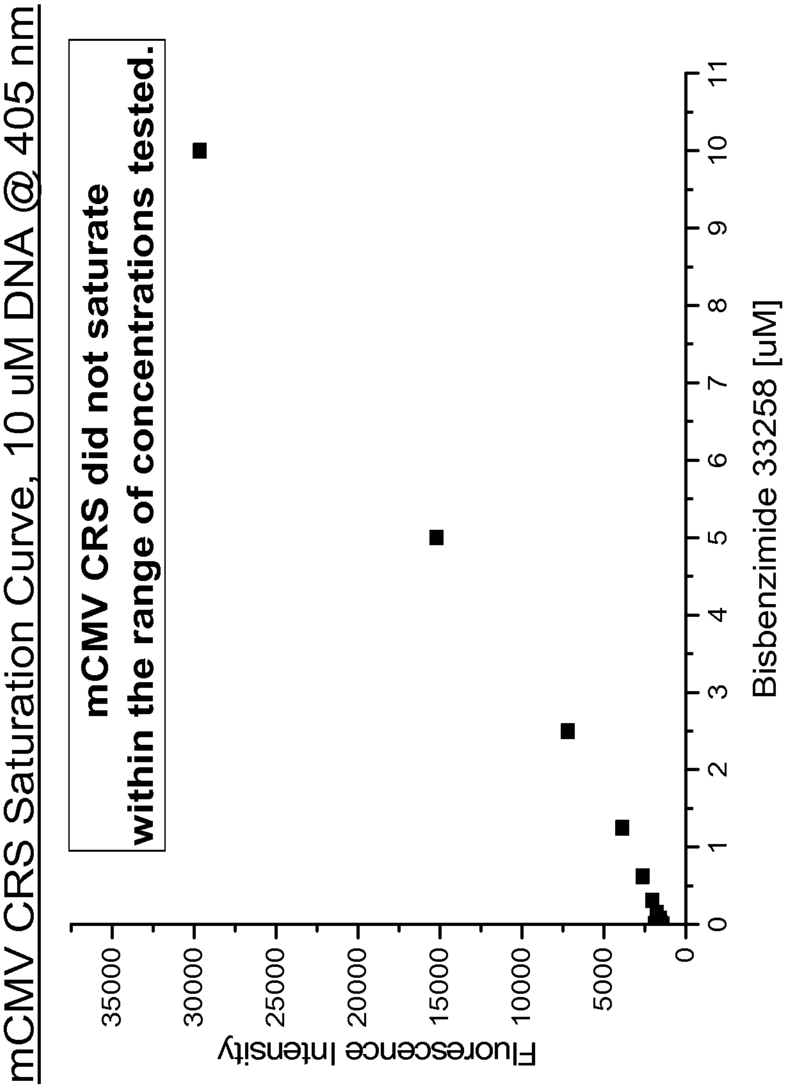
FIG. 18 provides a graph showing a bisBenzimide 33258 saturation curve for mCMV CRS sequence.
Figure 19:
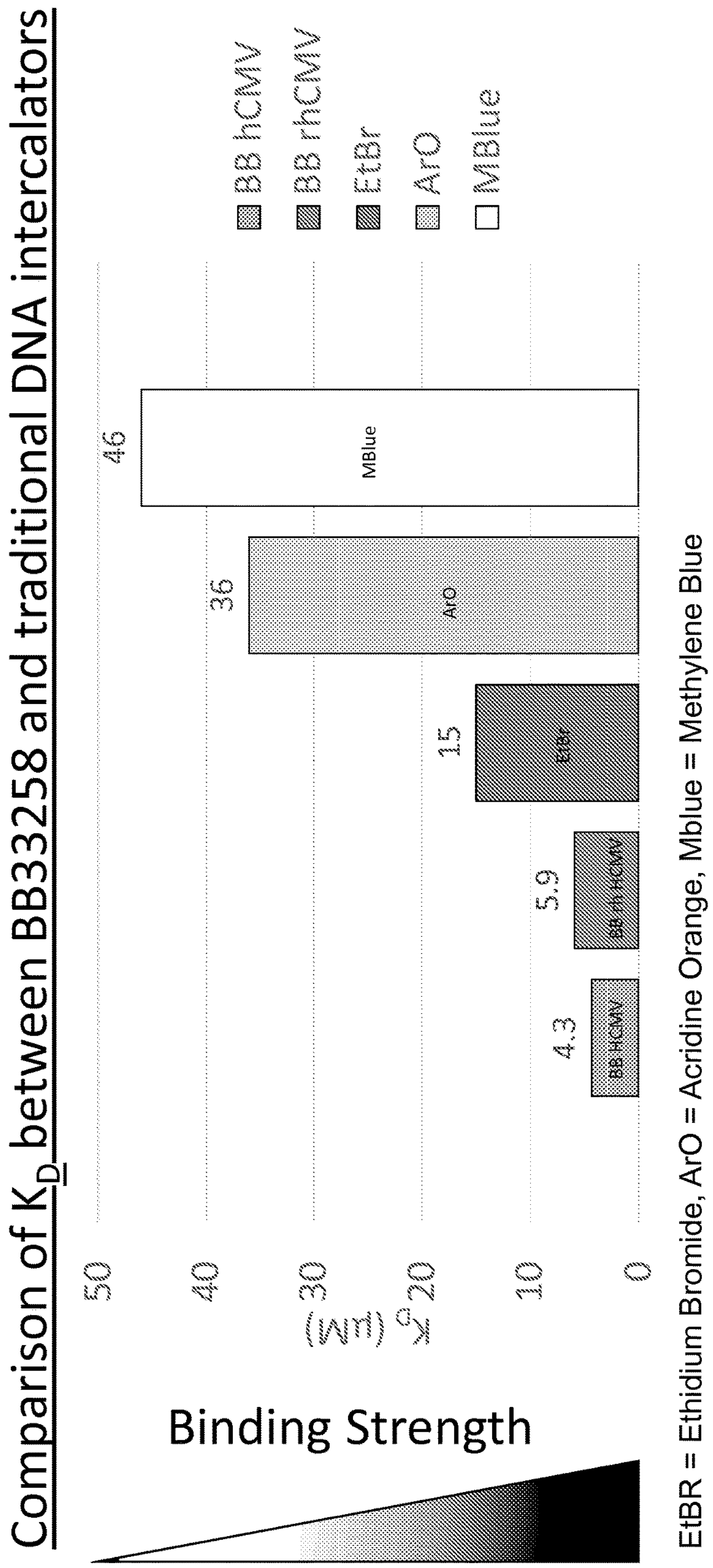
FIG. 19 provides a graph comparing binding strength ($K_d$) between BB33258 and traditional DNA intercalators, Ethidium Bromide, Acridine Orange, and Methylene Blue.

The results are shown in FIGS. 15-19. As shown in FIGS. 15 and 16 BB33258 binds primarily to a specific tetranucleotide motif (TTTA). FIG. 17 shows hCMV CRS and rHCMV CRS saturation curves. FIG. 18 provides a graphs showing that mCMV did not saturate within the range of concentrations tested. FIG. 19 provides a comparison of $K_d$ between BB33258 and traditional DNA intercalators.

Example 3: Gel Shift Assay of IE2-CRS

Materials and Methods

IE2-MBP expressed in BL21 cells was purified using amylose column, and EMSA was performed for IE2-crs interaction as described in Macias, M. P., Stinski, M. F., 1993. *PNAS.* 90, 707-711.

Results

Figure 20:
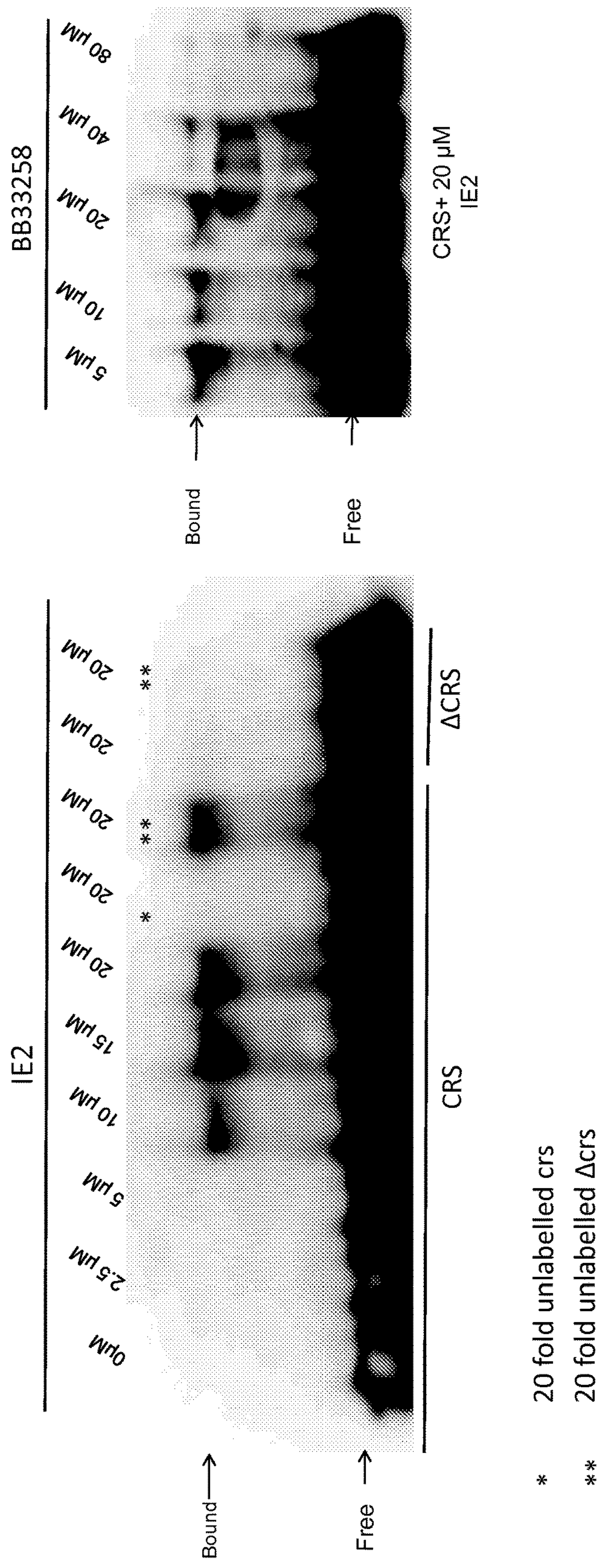
FIG. 20 provides images of gel results for electrophoretic mobility shift assays (EMSA) using purified IE2 protein and DNA CRS target in the presence of various amounts of BB33258.

The results are shown in FIG. 20, which provides images of gel results for electrophoretic mobility shift assays (EMSA) using purified IE2 protein and DNA CRS target in the presence of various amounts of BB33258. The gels demonstrate binding of BB33258 to the CRS sequence.

Example 4: Additional CMV Assays

Materials and Methods

Flow cytometry was performed on TB40E infected ARPE cells at 17 h and 20 h post infection. The data was analyzed as described in Teng et al. Cell 2012, cited herein.

Results

FIG. 21 provides data showing feedback inhibitor BB33258 breaks the IE2 circuit and amplifies IE2 expression levels in clinically derived CMV isolate TB40E.

FIG. 22 provides data showing feedback inhibitor BB33258 results in virus fitness loss for clinically derived CMV isolate TB40E. Detection of virus infection where IE2-YFP positive cells show drug treatment (right panel image) inhibits cell to cell spread. (Cells show more CPE with drug treatment and appear more distorted and larger.) Infection at MOI of 1 on confluent epithelial cell monolayers. Images on day 5, post infection.

FIG. 23 provides data showing Hoescht 33258 inhibits HCMV infection across a wide range of virus concentrations. All time points were taken at 10 days post-infection as described in Teng et al. Cell 2012 (cited herein).

REFERENCES

Bankier, A. T., Beck, S., Bohni, R., Brown, C. M., Cerny, R., Chee, M. S., Hutchison, C. A., 3rd, Kouzarides, T., Martignetti, J. A., Preddie, E., et al. (1991). The DNA sequence of the human cytomegalovirus genome. DNA Seq 2, 1-12.

Bolovan-Fritts, C., and Wiedeman, J. A. (2001). Human cytomegalovirus strain Toledo lacks a virus-encoded tropism factor required for infection of aortic endothelial cells. J Infect Dis 184, 1252-1261.

Bolovan-Fritts, C. A., Trout, R. N., and Spector, S. A. (2004). Human cytomegalovirus-specific CD4+-T-cell cytokine response induces fractalkine in endothelial cells. J Virol 78, 13173-13181.

Bresnahan, W. A., and Shenk, T. E. (2000). UL82 virion protein activates expression of immediate early viral genes in human cytomegalovirus-infected cells. Proc Natl Acad Sci USA 97, 14506-14511.

Cuevas-Bennett, C., and Shenk, T. (2008). Dynamic histone H3 acetylation and methylation at human cytomegalovirus promoters during replication in fibroblasts. J Virol 82, 9525-9536.

Dull, T., Zufferey, R., Kelly, M., Mandel, R. J., Nguyen, M., Trono, D., and Naldini, L. (1998). A third-generation lentivirus vector with a conditional packaging system. J Virol 72, 8463-8471.

Lilja, A. E., Chang, W. L., Barry, P. A., Becerra, S. P., and Shenk, T. E. (2008). Functional genetic analysis of rhesus cytomegalovirus: Rh01 is an epithelial cell tropism factor. J Virol 82, 2170-2181.

Meier, J. L. (2001). Reactivation of the human cytomegalovirus major immediate-early regulatory region and viral replication in embryonal NTera2 cells: role of trichostatin A, retinoic acid, and deletion of the 21-base-pair repeats and modulator. J Virol 75, 1581-1593.

Moorman, N. J., Cristea, I. M., Terhune, S. S., Rout, M. P., Chait, B. T., and Shenk, T. (2008). Human cytomegalovirus protein UL38 inhibits host cell stress responses by antagonizing the tuberous sclerosis protein complex. Cell Host Microbe 3, 253-262.

Nevels, M., Brune, W., and Shenk, T. (2004). SUMOylation of the human cytomegalovirus 72-kilodalton IE1 protein facilitates expression of the 86-kilodalton IE2 protein and promotes viral replication. J Virol 78, 7803-7812.

Orr, M. T., Murphy, W. J., and Lanier, L. L. (2010). 'Unlicensed' natural killer cells dominate the response to cytomegalovirus infection. Nat Immunol 11, 321-327.

Teng, M. W., Bolovan-Fritts, C., Dar, R. D., Womack, A., Simpson, M. L., Shenk, T., and Weinberger, L. S. (2012). An endogenous accelerator for viral gene expression confers a fitness advantage. Cell 151, 1569-1580.

Warming, S., Costantino, N., Court, D. L., Jenkins, N. A., and Copeland, N. G. (2005). Simple and highly efficient BAC recombineering using galK selection. Nucleic Acids Res 33, e36.

Yu, D., Smith, G. A., Enquist, L. W., and Shenk, T. (2002). Construction of a self-excisable bacterial artificial chromosome containing the human cytomegalovirus genome and mutagenesis of the diploid TRL/IRL13 gene. J Virol 76, 2316-2328.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method for inhibiting cytomegalovirus (CMV) replication in a cell infected with CMV, the method comprising contacting the cell with an effective amount of a bisbenzimidazole compound to inhibit CMV replication in the cell, wherein the bisbenzimidazole compound has the structure of formula (I)

(I)

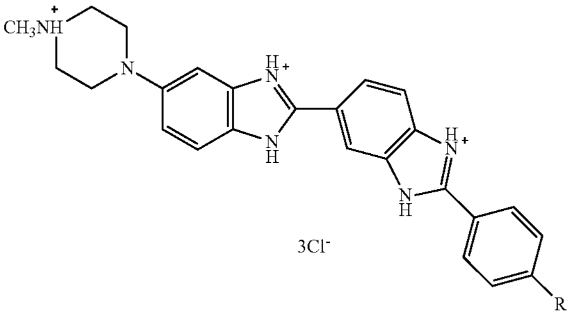

wherein:

R is OH, —O—$CH_2CH_3$ or $N(CH_3)_2$.

2. The method of claim 1, wherein the bisbenzimidazole compound is 2'-(4-hydroxyphenyl)-5-(4-methyl-1-piperazinyl)-2,5'-bi-1H-benzimidazole trihydrochloride hydrate.

3. The method of claim 1, wherein the bisbenzimidazole compound has the structure of formula (II)

(II)

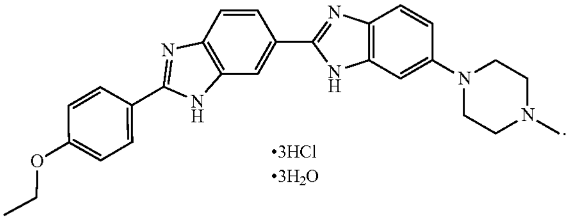

4. A method of treating a cytomegalovirus (CMV) infection in an individual, the method comprising administering to the individual an effective amount of a bisbenzimidazole compound to treat the CMV infection, wherein the bisbenzimidazole compound has the structure of formula (I)

(I)

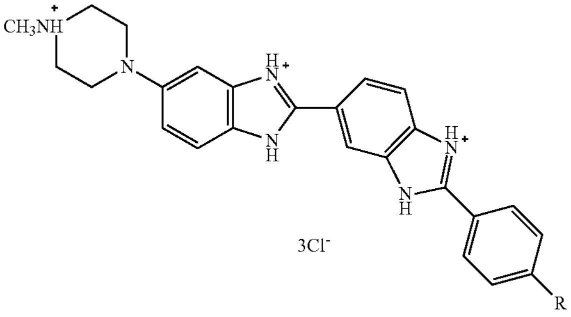

wherein:

R is OH, —O—$CH_2CH_3$ or $N(CH_3)_2$.

5. The method of claim 4, wherein the bisbenzimidazole compound is 2'-(4-hydroxyphenyl)-5-(4-methyl-1-piperazinyl)-2,5'-bi-1H-benzimidazole trihydrochloride hydrate.

6. The method of claim 4, wherein the bisbenzimidazole compound has the structure of formula (II)

(II)

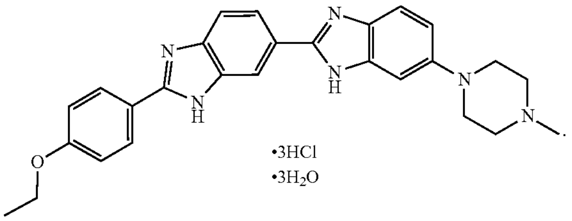

7. The method of claim 4, wherein the bisbenzimidazole compound is administered orally or intravenously.

8. The method of claim 4, wherein the bisbenzimidazole compound is administered at a dose of from 5 $mg/m^2$/day to 50 $mg/m^2$/day.

9. The method of claim 4, wherein the individual is a human.

10. The method of claim 4, comprising administering at least a second therapeutic agent.

11. The method of claim 10, wherein the second therapeutic agent is ganciclovir, foscarnet, cidofovir, maribavir, or valganciclovir.

12. The method of claim 10, wherein the second therapeutic agent is a histone deacetylase (HDAC) inhibitor.

13. The method of claim 10, wherein the second therapeutic agent is a transcriptional transactivator.

14. The method of claim 4, wherein the individual is an organ transplant recipient.

15. The method of claim 4, wherein the individual is a bone marrow transplant recipient.

16. The method of claim 4, wherein the individual does not have a CMV infection, and is an organ transplant recipient.

17. The method of claim 4, wherein the individual does not have a CMV infection, and is a bone marrow transplant recipient.

18. The method of claim 4, wherein the individual is a pregnant female.

19. The method of claim 4, wherein the individual is a neonate.

20. A method of inhibiting cytomegalovirus (CMV) replication in an organ or tissue, the method comprising contacting the organ or tissue in vitro or ex vivo with an effective amount of a bisbenzimidazole compound to inhibit CMV replication in the organ or tissue, wherein the bisbenzimidazole compound has the structure of formula (I)

(I)
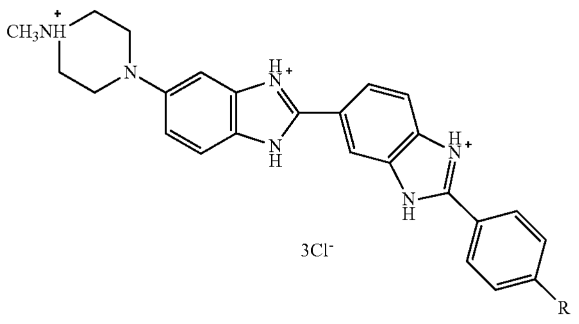
wherein:
R is OH, —O—$CH_2CH_3$ or $N(CH_3)_2$.
* * * * *

SEQUENCE LISTING

```
<160> NUMBER OF SEQ ID NOS: 9

<210> SEQ ID NO 1
<211> LENGTH: 14
<212> TYPE: DNA
<213> ORGANISM: Artificial sequence
<220> FEATURE:
<223> OTHER INFORMATION: nucleic acid sequence motif

<400> SEQUENCE: 1

tcgtttagtg aacc                                                    14


<210> SEQ ID NO 2
<211> LENGTH: 14
<212> TYPE: DNA
<213> ORGANISM: Artificial sequence
<220> FEATURE:
<223> OTHER INFORMATION: nucleic acid sequence motif

<400> SEQUENCE: 2

tcaggtagtg aacc                                                    14


<210> SEQ ID NO 3
<211> LENGTH: 14
<212> TYPE: DNA
<213> ORGANISM: Artificial sequence
<220> FEATURE:
<223> OTHER INFORMATION: nucleic acid sequence motif

<400> SEQUENCE: 3

tcgtttaggg aacc                                                    14


<210> SEQ ID NO 4
<211> LENGTH: 14
<212> TYPE: DNA
<213> ORGANISM: Artificial sequence
<220> FEATURE:
<223> OTHER INFORMATION: nucleic acid sequence motif

<400> SEQUENCE: 4

ccagcgtcgg tacc                                                    14


<210> SEQ ID NO 5
<211> LENGTH: 14
<212> TYPE: DNA
```

-continued

<213> ORGANISM: Artificial sequence
<220> FEATURE:
<223> OTHER INFORMATION: nucleic acid sequence motif

<400> SEQUENCE: 5
gcgcgcgcgc gcgc 14

<210> SEQ ID NO 6
<211> LENGTH: 14
<212> TYPE: DNA
<213> ORGANISM: Artificial sequence
<220> FEATURE:
<223> OTHER INFORMATION: nucleic acid sequence motif

<400> SEQUENCE: 6
cgcaaaattt tgcg 14

<210> SEQ ID NO 7
<211> LENGTH: 15
<212> TYPE: DNA
<213> ORGANISM: Artificial sequence
<220> FEATURE:
<223> OTHER INFORMATION: nucleic acid sequence motif

<400> SEQUENCE: 7
tcgtttagtg aaccg 15

<210> SEQ ID NO 8
<211> LENGTH: 15
<212> TYPE: DNA
<213> ORGANISM: Artificial sequence
<220> FEATURE:
<223> OTHER INFORMATION: nucleic acid sequence motif

<400> SEQUENCE: 8
tcgtttaggg aaccg 15

<210> SEQ ID NO 9
<211> LENGTH: 15
<212> TYPE: DNA
<213> ORGANISM: Artificial sequence
<220> FEATURE:
<223> OTHER INFORMATION: nucleic acid sequence motif

<400> SEQUENCE: 9
ccagcgtcgg taccg 15